United States Patent
Khademhosseini et al.

(10) Patent No.: US 10,814,032 B2
(45) Date of Patent: *Oct. 27, 2020

(54) ELASTIC BIOPOLYMER AND USE AS A TISSUE ADHESIVE

(71) Applicant: THE BRIGHAM AND WOMEN'S HOSPITAL, INC., Boston, MA (US)

(72) Inventors: Ali Khademhosseini, Cambridge, MA (US); Nasim Annabi, Cambridge, MA (US); Alexander Assmann, Cambridge, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 490 days.

This patent is subject to a terminal disclaimer.

(21) Appl. No.: 15/502,347

(22) PCT Filed: Aug. 6, 2015

(86) PCT No.: PCT/US2015/044022
§ 371 (c)(1),
(2) Date: Feb. 7, 2017

(87) PCT Pub. No.: WO2016/022807
PCT Pub. Date: Feb. 11, 2016

(65) Prior Publication Data
US 2017/0232138 A1 Aug. 17, 2017

Related U.S. Application Data

(60) Provisional application No. 62/034,973, filed on Aug. 8, 2014.

(51) Int. Cl.
*A61L 24/10* (2006.01)
*A61L 24/00* (2006.01)
*A61K 31/137* (2006.01)

(52) U.S. Cl.
CPC .......... *A61L 24/104* (2013.01); *A61K 31/137* (2013.01); *A61L 24/001* (2013.01); *A61L 24/0015* (2013.01); *A61L 24/0031* (2013.01); *A61L 2300/104* (2013.01); *A61L 2300/404* (2013.01); *A61L 2300/418* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 5,064,430 A | 11/1991 | Urry | |
| 5,674,623 A | 10/1997 | Haddon et al. | |
| 6,458,386 B1 | 10/2002 | Schacht et al. | |
| 6,585,873 B1 | 7/2003 | Solomon et al. | |
| 6,608,040 B1 | 8/2003 | Lin et al. | |
| 7,435,425 B2 | 10/2008 | Qian et al. | |
| 7,547,446 B2 | 6/2009 | Qian et al. | |
| 7,854,923 B2 | 12/2010 | Chen et al. | |
| 7,871,637 B2 | 1/2011 | Qian et al. | |
| 7,871,639 B2 | 1/2011 | Schankereli et al. | |
| 8,092,820 B2 | 1/2012 | Qian et al. | |
| 8,314,211 B2 | 11/2012 | Falus | |
| 8,383,141 B2 | 2/2013 | Qian et al. | |
| 8,513,217 B2 | 8/2013 | Chen et al. | |
| 9,066,991 B2 | 6/2015 | Preiss-Bloom et al. | |
| 9,084,728 B2 | 7/2015 | Goessl et al. | |
| 2004/0110439 A1 | 6/2004 | Chaikof et al. | |
| 2005/0112182 A1 | 5/2005 | Minami et al. | |
| 2008/0312156 A1 | 12/2008 | Setton et al. | |
| 2009/0175946 A1* | 7/2009 | Gaissmaier | A61P 17/02 424/484 |
| 2012/0128653 A1 | 5/2012 | Goessl et al. | |
| 2013/0172985 A1 | 7/2013 | Prestwich et al. | |
| 2014/0107065 A1 | 4/2014 | Chen et al. | |

(Continued)

FOREIGN PATENT DOCUMENTS

WO    WO-2015086640 A1 *  6/2015    ......... A61L 24/0005

OTHER PUBLICATIONS

Nichol, Jason W., et al. "Cell-laden microengineered gelatin methacrylate hydrogels." Biomaterials 31.21 (2010): 5536-5544.*
Elvin, Christopher M., et al. "A highly elastic tissue sealant based on photopolymerised gelatin." Biomaterials 31.32 (2010): 8323-8331.*
Mehdizadeh, Mohammadreza, and Jian Yang. "Design strategies and applications of tissue bioadhesives." Macromolecular bioscience 13.3 (2013): 271-288.*
Suzuki, S., and Y. Ikada. "Sealing effects of cross-linked gelatin." Journal of biomaterials applications 27.7 (2013): 801-810.*
Jun et al., "Comparison of Bursting Pressure after Scleral Tunnel Incision Sealed with Sutures or an Adherent Ocular Bandage in Human Globes", The Journal of International Medical Research 40:756-760 (2012).

(Continued)

*Primary Examiner* — Bethany P Barham
*Assistant Examiner* — Peter Anthopolos
(74) *Attorney, Agent, or Firm* — Fish & Richardson P.C.

(57) ABSTRACT

The present invention provides an improved tissue adhesive to repair defects in soft tissue. Following ASTM standard tests, crosslinked methacryloyl-substituted gelatin hydrogels of the present invention (GelSEAL) were shown to exhibit adhesive properties, i.e. wound closure strength, shear resistance and burst pressure, that were superior to clinically used fibrin- and poly(ethylene glycol)-based glues. Chronic in vivo experiments in rats proved GelSEAL to effectively seal large lung leakages without additional sutures or staples, presenting improved performance as compared to fibrin and poly(ethylene glycol) glues. Furthermore, subcutaneous implantation in rats revealed high biocompatibility of GelSEAL as evidenced by low inflammatory host response. Advantageously, the tissue adhesives of the present invention are low cost and easy to produce, making them a promising substance to be used as a sealant for fluid leakages in soft tissue, as well as an easily tunable platform to further optimize the adhesive characteristics.

13 Claims, 16 Drawing Sheets

(56) References Cited

U.S. PATENT DOCUMENTS

| | | |
|---|---|---|
| 2014/0377326 A1 | 12/2014 | Niu et al. |
| 2015/0037314 A1 | 2/2015 | Larsen |
| 2015/0209109 A1 | 7/2015 | Rege et al. |
| 2015/0291939 A1 | 10/2015 | Tomer et al. |

OTHER PUBLICATIONS

Katagiri et al., "All Six Modules of the Gelatin-binding Domain of Fibronectin Are Required for Full Affinity", The Journal of Biological Chemistry 278(14):11897-11902 (2003).

Kharazifia et al., "Tough and Flexible CNT—Polymeric Hybrid Scaffolds for Engineering Cardiac Constructs", Biomaterials 35(26):7346-7354 (2014).

Kim et al., "Self-Assembly of Thermally Responsive Amphiphilic Diblock Copolypeptides into Spherical Micellar Nanoparticles", Angewandte Chemie International Edition 49:4257-4260 (2010).

Kim et al., "Biomimetic Scaffolds for Tissue Engineering", Advanced Functional Materials 22:2446-2468 (2012).

Kobayashi et al., "In Vivo Evaluation of a New Sealant Material on a Rat Lung Air Leak Model", Journal of Biomedical Materials Research (Applied Biomaterials) 58:658-665 (2001).

Lai et al., "Gelatin methacrylate/carboxybetaine methacrylate hydrogels with tunable crosslinking for controlled drug release", Journal of Materials Chemistry B 4:2304-2313 (2016).

Leahey et al., "Clinical Experience with N-butyl Cyanoacryiate (Nexacryl) Tissue Adhesive", Ophthalmology 100(2):173-180 (1993).

Lee et al., "Hydrogels for Tissue Engineering", Chemical Reviews 101(7):1869-1879 (2001).

Li et al., "Toward a Stretchable, Elastic, and Electrically Conductive Nanocomposite: Morphology and Properties of Poly[styrene-b-(ethylene-co-butylene)-b-styrene]/Multiwalled Carbon Nanotube Composites Fabricated by High-Shear Processing", Macromolecules 42(7):2587-2593 (2009).

Lim et al., "Rapid Crosslinking of Elastin-like Polypeptides with Hydroxymethylphosphines in Aqueous Solution", Biomacromolecules 8(5):1463-1470 (2007).

Lynn et al., "Antigenicity and Immunogenicity of Collagen", Journal of Biomedical Materials Research Part B: Applied Biomaterials 71B:343-354 (2004).

Macewan et al., "Elastin-Like Polypeptides: Biomedical Applications of Tunable Biopolymers", Peptide Science 94(1):60-77 (2010).

Macewan et al., "Applications of elastin-like polypeptides in drug delivery", Journal of Controlled Release 190:314-330 (2014).

McHale et al., "Synthesis and in Vitro Evaluation of Enzymatically Cross-Linked Elastin-Like Polypeptide Gels for Cartilaginous Tissue Repair", Tissue Engineering 11(11/12):1768-1779 (2005).

Mehdizadeh et al., "Injectable citrate-based mussel-inspired tissue bioadhesives with high wet strength for sutureless wound closure", Biomaterials 33:7972-7983 (2012).

Meyer et al., "Purification of recombinant proteins by fusion with thermally-responsive polypeptides", Nature Biotechnology 17:1112-1115 (1999).

Montanaro et al., "Cytotoxicity, blood compatibility and antimicrobial activity of two cyanoacrylate glues for surgical use", Biomaterials 22:59-66 (2001).

Munoz et al., "Gelatin hydrogels formed by orthogonal thiol-norbornene photochemistry for cell encapsulation", Biomaterials Science 2:1063-1072 (2014).

Nagapudi et al., "Photomediated Solid-State Cross-Linking of an Elastin- Mimetic Recombinant Protein Polymer", Macromolecules 35(5):1730-1737 (2002).

Nakayama et al., "Enhancement of visible light-induced gelation of photocurable gelatin by addition of polymeric amine", Journal of Photochemistry and Photobiology A: Chemistry 177:205-211 (2006).

Nan et al., "Nosocomial Infection After Lung Surgery: Incidence and Risk Factors", Chest 128(4):2647-2652 (2005).

Nettles et al., "In Situ Crosslinking Elastin-Like Polypeptide Gels for Application to Articular Cartilage Repair in a Goat Osteochondral Defect Model", Tissue Engineering Part A 14(7):1133-1140 (2008).

Nettles et al., "Applications of Elastin-like Polypeptides in Tissue Engineering", Advanced Drug Delivery Reviews 62(15):1479-1485 (2010).

Nichol et al., "Cell-laden microengineered gelatin methacrylate hydrogels", Biomaterials 31:5536-5544 (2010).

Nikkhah et al., "Directed endothelial cell morphogenesis in micropatterned gelatin methacrylate hydrogels", Biomaterials 33:9009-9018 (2012).

Okajima et al., "Kinetics of volume phase transition in poly(N-isopropylacrylamide) gels", Journal of Chemical Physics 116(20):9068-9077 (2002).

Omidian et al., "Elastic, Superporous Hydrogel Hybrids of Polyacrylamide and Sodium Alginate", Macromolecular Bioscience 6:703-710 (2006).

Papatheofanis F., "Prothrombotic Cytotoxicity of Cyanoacrylate Tissue Adhesive", Journal of Surgical Research 47(4):309-312 (1989).

Park et al., "Evaluation of Polyethylene Glycol Based Hydrogel for Tissue Sealing After Laparoscopic Partial Nephrectomy in a Porcine Model", The Journal of Urology 172:2446-2450 (2004).

Paul et al., "Injectable Graphene Oxide/Hydrogel-Based Angiogenic Gene Delivery System for Vasculogenesis and Cardiac Repair", ACS Nano 8(8):8050-8062 (2014).

Qerimi et al., "Collagen hemostat significantly reduces time to hemostasis compared with cellulose: COBBANA, a single-center, randomized trial", The American Journal of Surgery 205(6):636-641 (2013).

Raphel et al., "Photoreactive elastin-like proteins for use as versatile bioactive materials and surface coatings", Journal of Materials Chemistry 22(37):19429-19437 (2012).

Rogers et al., "Materials and Mechanics for Stretchable Electronics", Science 327:1603-1607 (2010).

Shazly et al., "Viscoelastic adhesive mechanics of aldehyde-mediated soft tissue sealants", Biomaterials 29:4584-4591 (2008).

Shin et al., "Carbon Nanotube Reinforced Hybrid Microgels as Scaffold Materials for Cell Encapsulation", ACS Nano 6(1):362-372 (2012).

Shin et al., "Carbon-Nanotube-Embedded Hydrogel Sheets for Engineering Cardiac Constructs and Bioactuators", ACS Nano 7(3):2369-2380 (2013).

Siegal et al., "Surgical Removal of Cyanoacrylate Adhesive After Accidental Instillation in the Anterior Chamber", Ophthalmic Surgery 20(3):179-181 (1989).

Spotnitz et al., "Hemostats, sealants, and adhesives III: a new update as well as cost and regulatory considerations for components of the surgical toolbox", Transfusion 52:2243-2255 (2012).

Sun et al., "Highly stretchable and tough hydrogels", Nature 489(7414):133-136 (2012).

Tang et al., "Oxidatively Responsive Chain Extension to Entangle Engineered Protein Hydrogels", Macromolecules 47(2):791-799 (2014).

Teng et al., "Morphological analysis of leucocyte transmigration in the pleural cavity", Journal of Anatomy 203:391-404 (2003).

Tessmar et al., "Customized PEG-Derived Copolymers for Tissue-Engineering Applications", Macromolecular Bioscience 7:23-39 (2007).

Than et al., "Polyethylene Glycol Hydrogel Dural Sealant May Reduce Incisional Cerebrospinal Fluid Leak After Posterior Fossa Surgery", Operative Neurosurgery 63(ONS Suppl 1):ONS182-ONS187 (2008).

Trabbic-Carlson et al., "Swelling and Mechanical Behaviors of Chemically Cross-Linked Hydrogels of Elastin-like Polypeptides", Biomacromolecules 4(3):572-580 (2003).

Urry et al., "Biocompatibility of the Bioelastic Materials, Poly(GVGVP) and Its γ-Irradiation Cross-Linked Matrix: Summary of Generic Biological Test Results", Journal of Bioactive and Compatible Polymers 6:263-282 (1991).

Visser et al., "Endochondral bone formation in gelatin methacrylamide hydrogel with embedded cartilage-derived matrix particles", Biomaterials 1-9 (2014).

(56) References Cited

OTHER PUBLICATIONS

Wang et al., "A tough biodegradable elastomer", Nature Biotechnology 20:602-606 (2002).
Weiss et al., "The Use of Tissue Adhesive in Corneal Perforations", Ophthalmology 90(6):610-615 (1983).
Welsh et al., "Engineering the Extracellular Matrix: A Novel Approach to Polymeric Biomaterials. I. Control of the Physical Properties of Artificial Protein Matrices Designed to Support Adhesion of Vascular Endothelial Cells", Biomacromolecules 1(1)23-30 (2000).
Allen et al., "Prospective Randomized Study Evaluating a Biodegradable Polymeric Sealant for Sealing Intraoperative Air Leaks That Occur During Pulmonary Resection", The Annals of Thoracic Surgery 77:1792-1801 (2004).
Alleyne et al., "Efficacy and biocompatibility of a photopolymerized, synthetic, absorbable hydrogel as a dural sealant in a canine craniotomy model", Journal of Neurosurgery 88:308-313 (1998).
Anegg et al., "Efficiency of fleece-bound sealing (TachoSil®) of air leaks in lung surgery: a prospective randomised trial", European Journal of Cardio-thoracic Surgery 31:198-202 (2007).
Annabi et al., "The fabrication of elastin-based hydrogels using high pressure $CO_2$", Biomaterials 30:1-7 (2009).
Annabi et al., "Synthesis of highly porous crosslinked elastin hydrogels and their interaction with fibroblasts in vitro", Biomaterials 30:4550-4557 (2009).
Annabi et al., "Cross-linked open-pore elastic hydrogels based on tropoelastin, elastin and high pressure $CO_2$", Biomaterials 31:1655-1665 (2010).
Annabi et al., "Highly Elastic Micropatterned Hydrogel for Engineering Functional Cardiac Tissue", Advanced Functional Materials 23:4950-4959 (2013).
Annabi et al., "Engineered cell-laden human protein-based elastomer", Biomaterials 34(22):5496-5505 (2013).
Annabi et al., "25th Anniversary Article: Rational Design and Applications of Hydrogels in Regenerative Medicine", Advanced Materials 26(1):85-124 (2014).
Annabi et al., "Surgical Materials: Current Challenges and Nano-enabled Solutions", Nano Today 9(5):574-589 (2014).
Anselmo et al., "Platelet-like Nanoparticles: Mimicking Shape, Flexibility, and Surface Biology of Platelets to Target Vascular Injuries", ACS Nano 8(11):11243-11253 (2014).
Assmann et al., "The degeneration of biological cardiovascular prostheses under pro-calcific metabolic conditions in a small animal model", Biomaterials 1-13 (2014).
Baldock et al., "Shape of tropoelastin, the highly extensible protein that controls human tissue elasticity", Proceedings of the National Academy of Sciences 108(11):4322-4327 (2011).
Baranoski S., "Choosing a wound dressing, part 1", Nursing2008 60-61 (2008).
Bertassoni et al., "Hydrogel Bioprinted Microchannel Networks for Vascularization of Tissue Engineering Constructs", Lab on a Chip 14(13):2202-2211 (2014).
Betre et al., "Chondrocytic differentiation of human adipose-derived adult stem cells in elastin-like polypeptide", Biomaterials 27:91-99 (2006).
Bitton et al., "Phloroglucinol-based biomimetic adhesives for medical applications", Acta Biomaterialia 5:1582-1587 (2009).
Bottcher-Haberzeth et al., "Tissue engineering of skin", Burns 36:450-460 (2010).
Buckley et al., "Silver carbonate nanoparticles stabilised over alumina nanoneedles exhibiting potent antibacterial properties", Chemical Communications 4013-4015 (2008).
Buskens et al., "The use of a surgical sealant (CoSeal®) in cardiac and vascular reconstructive surgery: an economic analysis", The Journal of Cardiovascular Surgery 47(2):161-170 (2006).
Camci-Unal et al., "Synthesis and Characterization of Hybrid Hyaluronic Acid-Gelatin Hydrogels", Biomacromolecules 14(4):1085-1092 (2013).
Carlson et al., "Giant Papillary Conjunctivitis Associated With Cyanoacrylate Glue", American Journal of Ophthalmology 104(4):437-438 (1987).
Carrico et al., "Lithographic Patterning of Photoreactive Cell-Adhesive Proteins", Journal of the American Chemical Society 129(16):4874-4875 (2007).
Cavanaugh et al., "Infectious Keratitis and Cyanoacrylate Adhesive", American Journal of Ophthalmology 111(4):466-472 (1991).
Cha et al., "Controlling Mechanical Properties of Cell-Laden Hydrogels by Covalent Incorporation of Graphene Oxide", Small 10(3):514-523 (2014).
Charati et al., "Hydrophilic elastomeric biomaterials based on resilin-like polypeptides", Soft Matter 5(18):3412-3416 (2009).
Chen et al., "Functional Human Vascular Network Generated in Photocrosslinkable Gelatin Methacrylate Hydrogels", Advanced Functional Materials 22(10):2027-2039 (2012).
Chen et al., "Layer-by-Layer Bioprinting of Stem Cells for Retinal Tissue Regeneration", University of California, San Diego (2016). (22 pages).
Chou et al., "Genetically encoding an aliphatic diazirine for protein photocrosslinking", Chemical Science 2:480-483 (2011).
Costa et al., "Stimuli-Responsive Thin Coatings Using Elastin-Like Polymers for Biomedical Applications", Advanced Functional Materials 19:3210-3218 (2009).
Deacon et al., "Antimicrobial efficacy of tobramycin polymeric nanoparticles for Pseudomonas aeruginosa infections in cystic fibrosis: formulation, characterisation and functionalisation with dornase alfa (DNase)", Journal of Controlled Release (2015). (16 pages).
Debelle et al., "Elastin: molecular description and function", The International Journal of Biochemistry & Cell Biology 31:261-272 (1999).
Di Zio et al., "Mechanical Properties of Artificial Protein Matrices Engineered for Control of Cell and Tissue Behavior", Macromolecules 36(5):1553-1558 (2003).
Elvin et al., "A highly elastic tissue sealant based on photopolymerised gelatin", Biomaterials 31:8323-8331 (2010).
Elzoghby A., "Gelatin-based nanoparticles as drug and gene delivery systems: Reviewing three decades of research", Journal of Controlled Release 172:1075-1091 (2013).
Fogle et al., "Tissue Adhesive Arrests Stromal Melting in the Human Cornea", American Journal of Ophthalmology 89(6):795-802 (1980).
Foo et al., "Two-component protein-engineered physical hydrogels for cell encapsulation", Proceedings of the National Academy of Sciences 106(52):22067-22072 (2009).
Gaharwar et al., "Shear-Thinning Nanocomposite Hydrogels for the Treatment of Hemorrhage", ACS Nano 8(10):9833-9842 (2014).
Galler et al., "Self-assembling Multidomain Peptide Hydrogels: Designed Susceptibility to Enzymatic Cleavage Allows Enhanced Cell Migration and Spreading", Journal of the American Chemical Society 132(9):3217-3223 (2010).
Giannandrea et al., "Diverse functions of matrix metalloproteinases during fibrosis", Disease Models & Mechanisms 7:193-203 (2014).
Glickman et al., "A Polymeric Sealant Inhibits Anastomotic Suture Hole Bleeding More Rapidly Than Gelfoam/Thrombin: Results of a Randomized Controlled Trial", Archives of Surgery 137:326-331 (2002).
Gorgieva et al., "Collagen- vs. Gelatine-Based Biomaterials and Their Biocompatibility: Review and Perspectives", Biomaterials Applications for Nanomedicine, InTech (2011). (38 pages).
Hassan et al., "Smart copper oxide nanocrystals: Synthesis, characterization, electrochemical and potent antibacterial activity", Colloids Surfaces B: Biointerfaces 97:201-206 (2012).
He et al., "Polymorphisms in the Human Tropoelastin Gene Modify In Vitro Self-Assembly and Mechanical Properties of Elastin-Like Polypeptides", PLOS ONE 7(9):e46130 (2012). (12 pages).
Hida et al., "Retinal Toxicity of Cyanoacrylate Tissue Adhesive in the Rabbit", Retina 8:148-153 (1988).
Hjortnaes et al., "Directing Valvular Interstitial Cell Myofibroblast-Like Differentiation in a Hybrid Hydrogel Platform", Advanced Healthcare Materials 4:121-130 (2015).
Hrabchak et al., "Assessment of biocompatibility and initial evaluation of genipin cross-linked elastin-like polypeptides in the treatment of an osteochondral knee defect in rabbits", Acta Biomaterialia 6:2108-2115 (2010).

(56) References Cited

OTHER PUBLICATIONS

Huang et al., "Generation of Synthetic Elastin-Mimetic Small Diameter Fibers and Fiber Networks", Macromolecules 33(8):2989-2997 (2000).

Ifkovits et al., "Review: Photopolymerizable and Degradable Biomaterials for Tissue Engineering Applications", Tissue Engineering 13(10):2369-2385 (2007).

Itano H., "The optimal technique for combined application of fibrin sealant and bioabsorbable felt against alveolar air leakage", European Journal of Cardio-thoracic Surgery 33:457-460 (2008).

Wissink et al., "Immobilization of heparin to EDC/NHS-crosslinked collagen. Characterization and in vitro evaluation", Biomaterials 22:151-163 (2001).

Wolbank et al., "Non-invasive in vivo tracking of fibrin degradation by fluorescence imaging", Journal of Tissue Engineering and Regenerative Medicine 9:973-976 (2015).

Xia et al., "Tunable Self-Assembly of Genetically Engineered Silk-Elastin-Like Protein Polymers", Biomacromolecules 12(11):3844-3850 (2011).

Xia et al., "Nano-structured smart hydrogels with rapid response and high elasticity", Nature Communications 4:2226 (2013). (11 pages).

Xu et al., "Rheological Properties of Cysteine-Containing Elastin-Like Polypeptide Solutions and Hydrogels", Biomacromolecules 13(8):2315-2321 (2012).

Yue et al., "Synthesis, properties, and biomedical applications of gelatin methacryloyl (GelMA) hydrogels", Biomaterials 73:254-271 (2015).

Zhang et al., "Artificial Polypeptide Scaffold for Protein Immobilization", Journal of the American Chemical Society 127(29):10136-10137 (2005).

Zhao et al. "Photocrosslinkable Gelatin Hydrogel for Epidermal Tissue Engineering", Advanced Healthcare Materials 5(1)108-118 (2016).

Zhou et al., "Biomimetic mineralization of anionic gelatin hydrogels: effect of degree of methacrylation", RSC Advances 4:21997-22008 (2014).

Zhu et al., "Design properties of hydrogel tissue-engineering scaffolds", Expert Review of Medical Devices 8(5):607-626 (2011).

Glassman et al., "End block design modulates the Assembly and Mechanics of Thermoresponsive, Dual-Associative Protein Hydrogels", Macromolecules 48(6): 1832-1842 (2015).

Zhang et al., "A Highly Elastic and Rapidly Crosslinkable Elastin-Like Polypeptide-Based Hydrogel for Biomedical Applications", Advanced Functional Material 25(30): 4814-4826 (2015).

\* cited by examiner

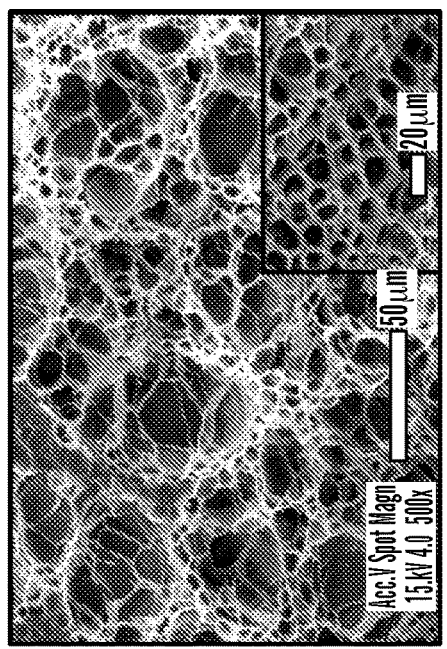
FIG. 1F
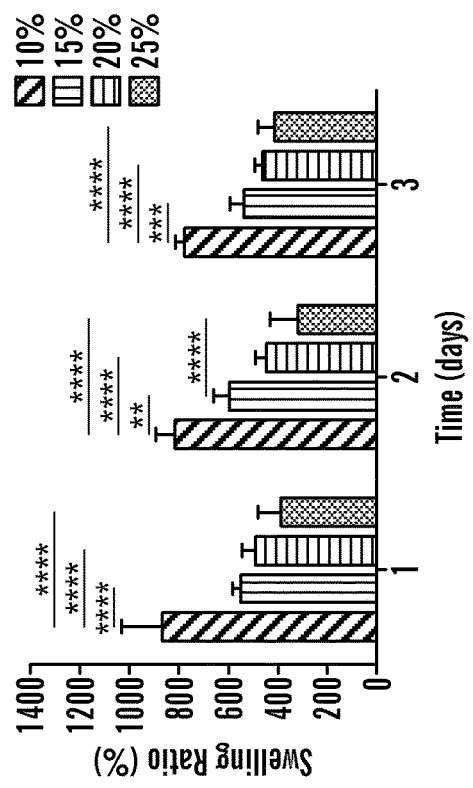
FIG. 1E
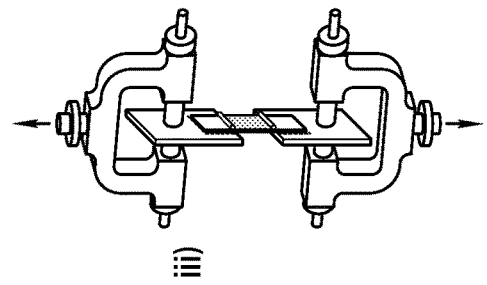
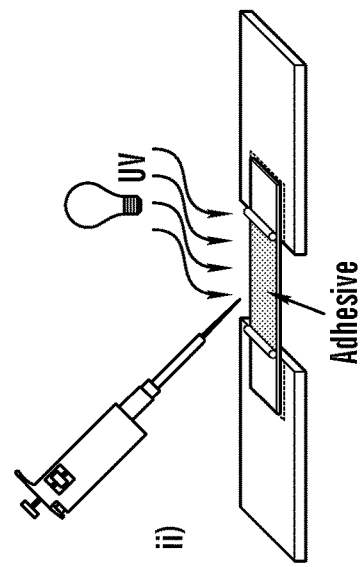
FIG. 2A
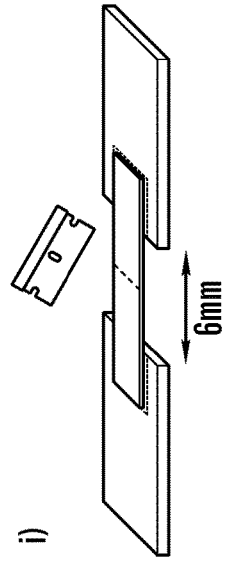

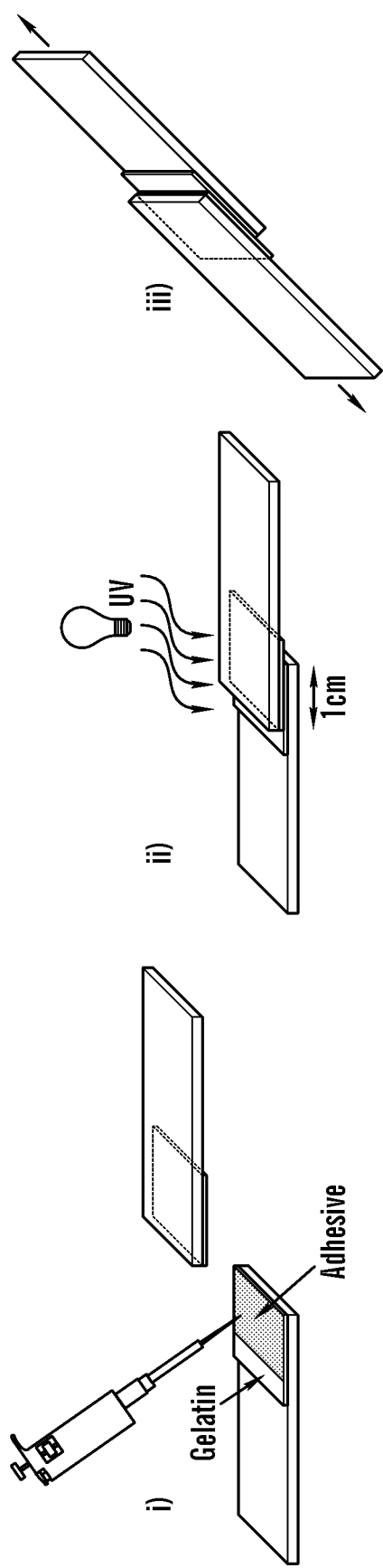
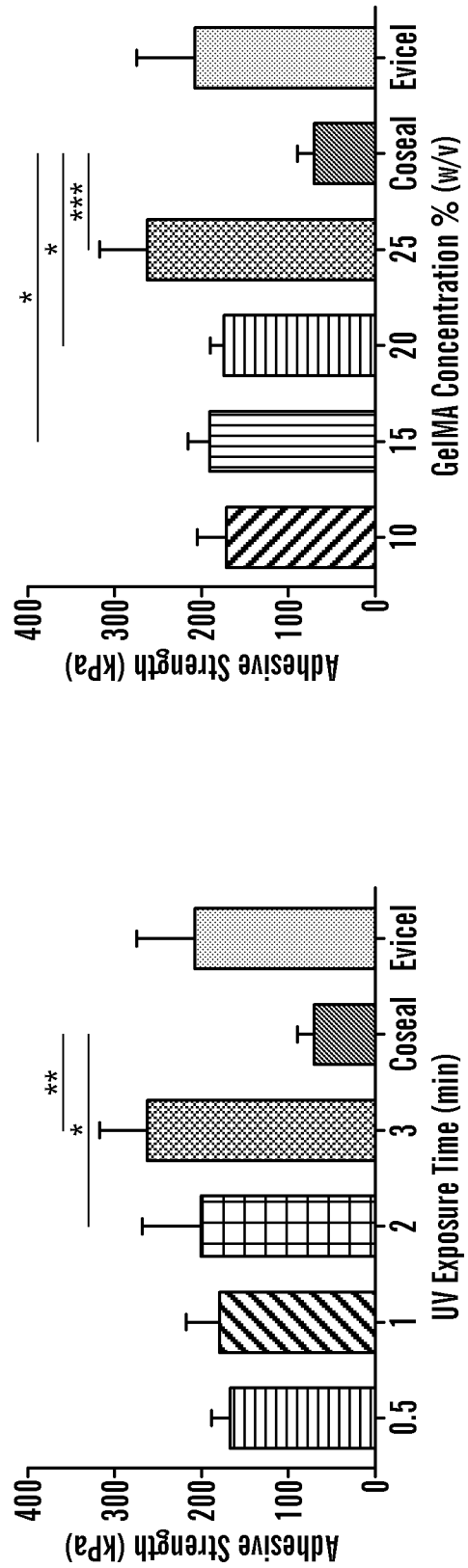
FIG. 3A
FIG. 3B
FIG. 3C

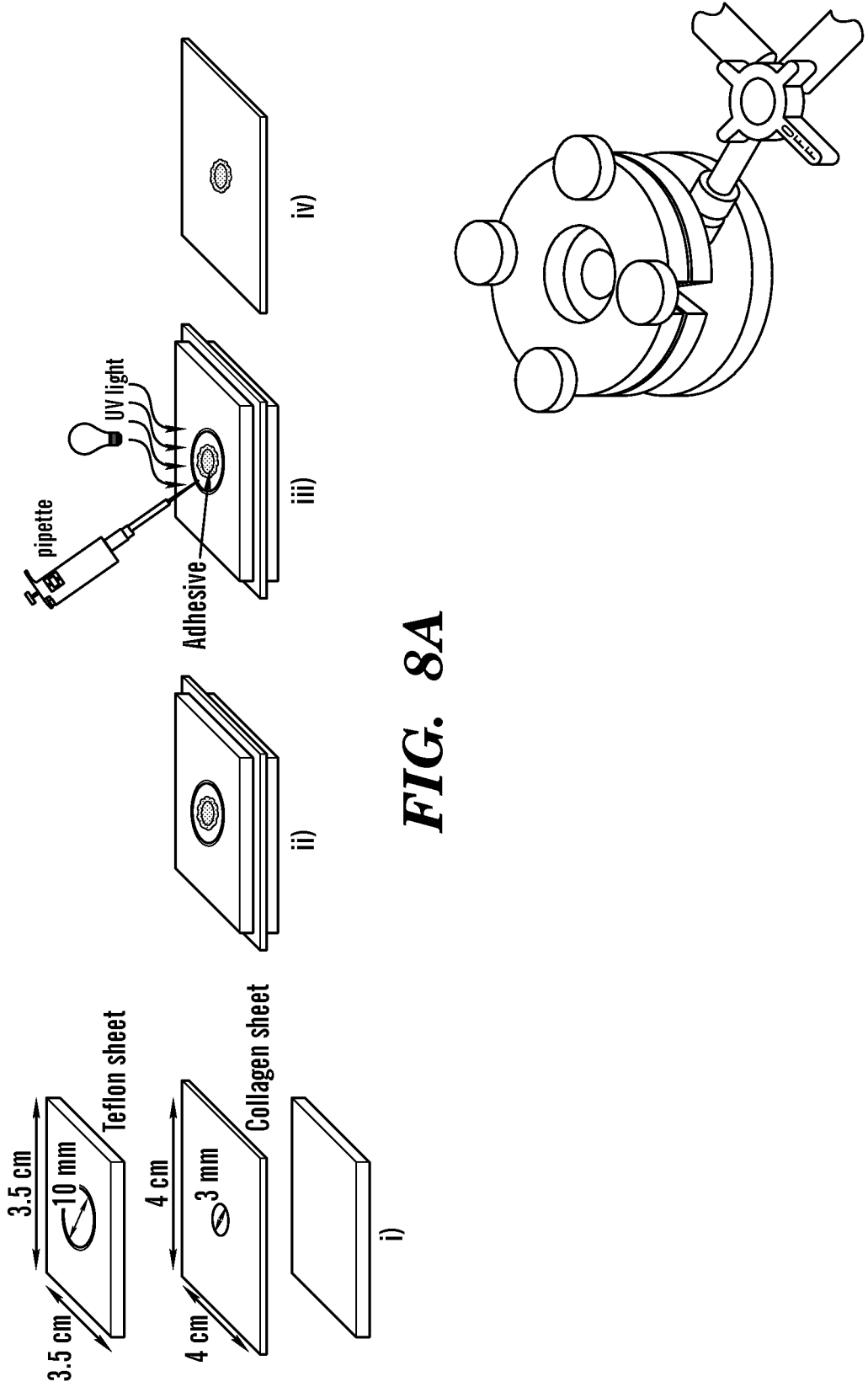

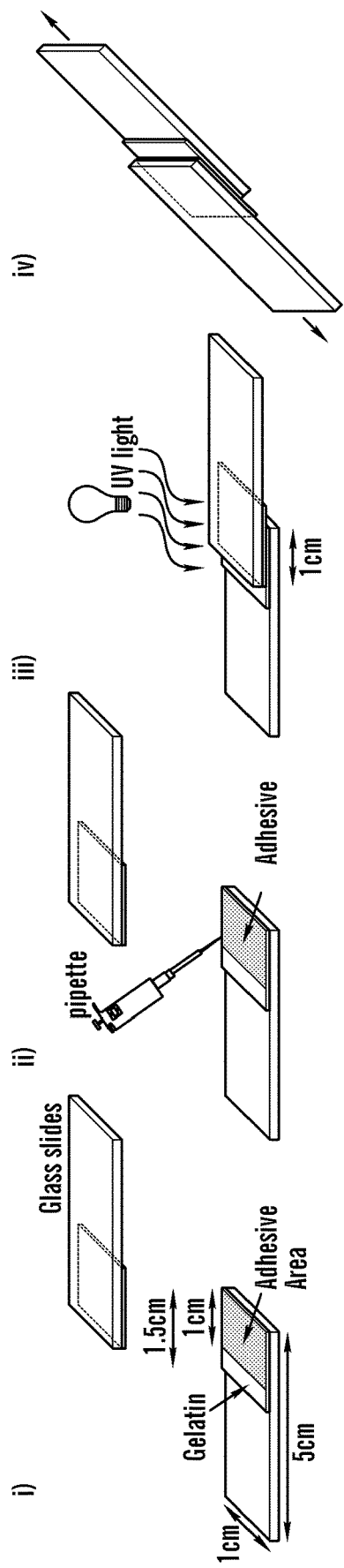
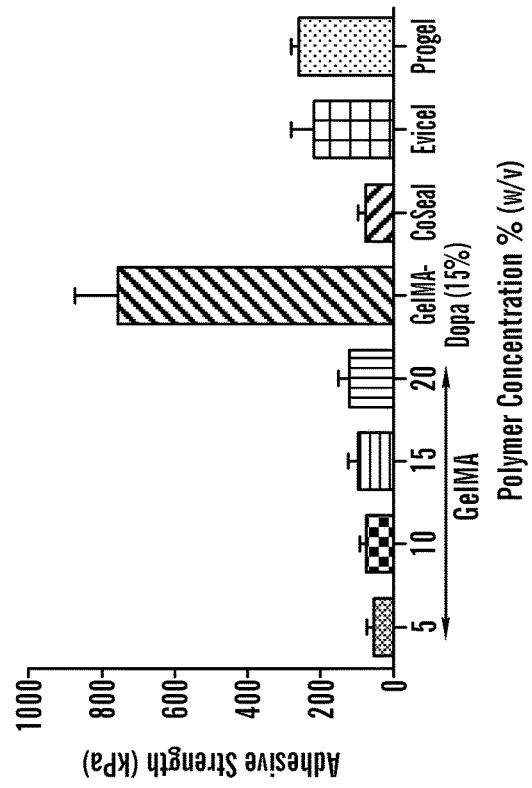
FIG. 10A
FIG. 10B

ELASTIC BIOPOLYMER AND USE AS A TISSUE ADHESIVE

CROSS REFERENCE TO RELATED APPLICATIONS

This application is a 371 National Phase Entry of International Patent Application No. PCT/US2015/044022 filed Aug. 6, 2015 which claims the benefit under 35 U.S.C. § 119(e) of U.S. Provisional Application Ser. No. 62/034,973, filed Aug. 8, 2014, the contents of which are incorporated herein by reference in their entirety.

GOVERNMENT SUPPORT

This invention was made with Government support under Grant Number DE021468 awarded by the National Institutes of Health. The Government has certain rights in this invention.

FIELD OF THE DISCLOSURE

The field of the disclosure relates to improved tissue adhesives and sealants for use in repairing soft tissue lesions. These tissue adhesives comprise elastic biopolymers which are biocompatible and biodegradable, and also have superior mechanical properties compared to commercially available tissue adhesives.

BACKGROUND

While traditional surgical treatment of tissue defects is achieved by sutures, staples or wires, the application of adhesives for a multitude of types of lesions is emerging. Particularly, the repair of parenchymatous defects, as e.g. in lung, liver or kidney, is a challenge, since the tissue consistency does not facilitate strong fastening of sutures or staples. In case of the lung, the fast and repetitively varying stress exerted by respiration provokes additional risk of failure of repair, which is further complicated by the non-sterile environment in the pulmonary airways, favoring wound infection [ITANO]. But even in tissues that can be technically sutured, accessory usage of adhesives may be necessary, as e.g. to seal small stitching channels in a sutured artery wall [GLICKMAN]. Furthermore, limited access to defect sites, as e.g. in the brain or during minimally invasive surgery, aggravates the problem of conventional suturing, which may be solved by applying adequate adhesives that polymerize on site [ANNABI 2014].

Damage to delicate soft tissue, such as lung tissue, is particularly challenging to repair. Lung tissue that has been punctured by biopsy or injury must be sealed surgically, using sutures, staples, or the implantation of a surgical mesh. However, these operations are time- and skill-intensive, and many post-surgical complications can occur, including infection due to incomplete wound sealing, tissue damage and scarring. Sutures and staples also do not effectively repair other membranous or elastic tissues, including the dura mater, urethral defects and bladder tissue. In some patients, lung tissue is so fragile that surgeons prefer to use an adhesive sealant instead of, or in addition to, the standard surgical closure methods to stop air leakage. Although several tissue adhesives are commercially available, none are ideal surgical sealants for repairing delicate soft tissues. Achieving significant adhesion to soft tissues while minimizing tissue damage poses a considerable clinical challenge. Cyanoacrylate, for example, is strongly adhesive, but its degradation products can induce an intense inflammatory response and it is not recommended to use for internal sealing. Fibrin glues on the other hand are more biocompatible, but they have low adhesive strength, particularly to wet tissues, and poor cohesive properties. Additional limitations of commercial tissue sealants include: high cost, limited availability, and, in some cases, long curing times of the adhesive. Therefore, there is an unmet need for an inexpensive, biocompatible tissue sealant with strong adhesion strength and high elasticity to repair delicate soft tissues, such as lung tissue.

In order to reach clinical applicability, adhesive candidate substances have to prove a couple of necessary properties. Independently on the purpose, a sufficient adhesive requires strong adhesive strength to the tissue to be repaired, not only to initially close the defect, but also to allow for subsequent wound healing. During this process, controlled degradation of the implanted adhesive is desirable [WOLBANK]. At least, the material should be biocompatible enough to avoid relevant inflammatory host response [MONTANARO]. Furthermore, most clinical applications require adhesives that polymerize under wet conditions. Economic aspects to be considered include application and curing within a reasonable period of time as well as cheap and safe production of the substance [SPOTNITZ]. Besides these general requirements, further demands occur depending on the target tissue. For example, defects in highly vascularized tissues require adhesives with hemostatic properties, air or liquid leakages necessitate effective sealants, and lesions in flexible tissues should be treated with elastic adhesives to preserve the functionality. Thus, different defect scenarios in different tissues require different adhesives with targeted properties.

The repertoire of available surgical adhesives comprises biological, synthetic and semi-synthetic substances. The most commonly used biological adhesives are fibrin- and/or collagen-based adhesives. Major drawbacks are modest mechanical characteristics, as well as high production costs and risk of contamination, both resulting from the biological source of the materials [BITTON, MEHDIZADEH]. Synthetic adhesives, especially the clinically used cyanoacrylates, provide low biocompatibility and biodegradability, evoke relevant foreign body response or even necrosis by toxic degradation products, and therefore, their usage is predominantly limited to external applications on the skin [BITTON, MEHDIZADEH]. Moreover, their adherence is restricted to dry tissue surfaces.

Human fibrin-based glues are probably the most widely used surgical adhesives, since they provide adequate hemostasis in many surgical scenarios and low immunogenicity. For example, Evicel® is a commercially available adhesive comprising fibrinogen and thrombin. Unfortunately, the mechanical characteristics of fibrin-based glues are limited, their production is expensive, and their human origin potentially allows for viral transmission of diseases like hepatitis C or human immunodeficiency virus [MEHDIZADEH].

Polymeric hydrogels are promising candidates to crosslink even under wet conditions and to serve as fluid barriers. Predominantly poly(ethylene glycol) (PEG) formulations have been tested as adhesives in vitro and in vivo so far [PARK, THAN, SHAZLY]. For example, CoSeal™ is a commercially available surgical sealant comprising PEG powder mixed with sodium phosphate buffer to produce a hydrogel. That unmodified poly(ethylene glycol) is non-immunogenic, favors its in vivo application, whereas the inert properties also avoid ingrowth of wound healing tissue [TES SMAR]. But due to limited mechanical characteristics, clinical indications for these adhesives are currently focused on sealing of suture line bleeding [BUSKENS].

Previously, a polymer composed of human serum albumin and a poly(ethylene glycol) derivative (Progel®) has been approved by the Food and Drug Administration for the intraoperative application during pulmonary resection. In a rat model, it had been shown that Progel® increases the lung burst pressure after sealing of a defect, when compared to fibrin glue [KOBAYASHI]. A multicenter trial in pulmonary resection patients showed that additional Progel® application was superior to suturing/stapling only [ALLEN]. The length of hospital stay was reduced by one day, and after 30 days, 35% of the Progel®-treated lungs were leak-free (versus 14% in the control group). Although this difference was statistically significant, 65% remaining or re-occurring leaks leave a lot of room to improve the air leakage sealing technique. The major drawbacks of Progel® are the high manufacturing costs due to extraction and purification of human serum albumin or production of the recombinant type, respectively. However, Progel® with recombinant albumin, the use of which is not approved in the US yet, eliminates the risk of transmitting human-pathogenic viruses.

Photopolymerization of methacryloyl-substituted gelatin is an inexpensive and technically simple approach to fabricate hydrogels for biomedical applications [CHA, NICHOL, SHIN, VIS SER]. The cytocompatibility of methacryloyl-substituted gelatin has been previously proven, suggesting it has potential to be implanted into a living organism [HJORTNAES, NIKKAH]. However, its actual function as a surgical material has not been evaluated yet in vivo. Moreover, the mechanical properties of methacryloyl-substituted gelatin have not been investigated, so it is unknown if it is suitable to serve as a tissue adhesive.

SUMMARY

Certain aspects of the present invention are directed to a tissue adhesive comprising a light activated methacryloyl-substituted gelatin, a photoinitiator and a pharmaceutically acceptable carrier. In some embodiments, the methacryloyl-substituted gelatin has a degree of methacrylation between 50% and 90%, 60% and 85%, or 70% and 80%. In some embodiments, the methacryloyl-substituted gelatin is present at a concentration between 10% and 40% (w/v), 15% and 35% (w/v), 20% and 30% (w/v), or 25% (w/v). In some embodiments, the tissue adhesive further comprises a hemostatic agent selected from the group consisting of blood coagulation factors, prothrombin, thrombin, silicate nanoparticles, etc. In some embodiments, the tissue adhesive further comprises an antibacterial agent selected from the group consisting of silver nanoparticles, copper oxide nanoparticles, nanoparticle-carried antibiotic drugs, penicillins, cephalosporins, penems, carbapenems, monobactams, aminoglycosides, sulfonamides, macrolides, tetracycline, lincosides, quinolones, chloramphenicol, vancomycin, metronidazole, rifampin, isoniazid, spectinomycin, trimethoprim sulfamethoxazole, chitosan, etc. In some embodiments, the photoinitiator is selected from the group consisting of 1-[4-(2-hydroxyethoxy)-phenyl]-2-hydroxy-2-methyl-1-propane-1-one, azobisisobutyronitrile, benzoyl peroxide, di-tert-butyl peroxide, 2,2-dimethoxy-2-phenylacetophenone, Eosin Y, etc. In some embodiments, the pharmaceutically acceptable carrier is selected from the group consisting of phosphate-buffered saline, water, etc.

In some embodiments, the methacryloyl-substituted gelatin further comprises dopamine conjugated to the gelatin. In some embodiments, the methacryloyl-substituted, dopylated gelatin has a degree of dopylation between 5% and 15%, or 10%. In some embodiments, the methacryloyl-substituted, dopylated gelatin is present at a concentration between 5% and 25% (w/v), 10% and 20% (w/v), or 15% (w/v).

Certain aspects of the present invention are directed to a tissue adhesive comprising a crosslinked methacryloyl-substituted gelatin hydrogel and a pharmaceutically acceptable carrier, wherein the crosslinked methacryloyl-substituted gelatin hydrogel has a degree of methacryloyl substitution between 50% and 90% and a concentration between 10% and 40% (w/v) in the pharmaceutically acceptable carrier. In some embodiments, the methacryloyl-substituted gelatin hydrogel has a degree of methacryloyl substitution between 60% and 85% and a concentration between 20% and 30% (w/v). In some embodiments, the methacryloyl-substituted gelatin hydrogel has a degree of methacryloyl substitution between 70% and 80% and a concentration of 25% (w/v). In some embodiments, the tissue adhesive has a wound closure strength of ≥20 kPa, ≥40 kPa, or ≥50 kPa. In some embodiments, the tissue adhesive has a shear resistance strength of ≥200 kPa, ≥250 kPa, or ≥300 kPa. In some embodiments, the tissue adhesive has a burst pressure of ≥5 kPa, ≥10 kPa, or ≥15 kPa. In some embodiments, the tissue adhesive further comprises a hemostatic agent selected from the group consisting of blood coagulation factors, prothrombin, thrombin, silicate nanoparticles, etc. In some embodiments, the tissue adhesive further comprises an antibacterial agent selected from the group consisting of silver nanoparticles, copper oxide nanoparticles, nanoparticle-carried antibiotic drugs, penicillins, cephalosporins, penems, carbapenems, monobactams, aminoglycosides, sulfonamides, macrolides, tetracycline, lincosides, quinolones, chloramphenicol, vancomycin, metronidazole, rifampin, isoniazid, spectinomycin, trimethoprim sulfamethoxazole, chitosan, etc.

In some embodiments, the methacryloyl-substituted gelatin hydrogel further comprises dopamine conjugated to the gelatin. In some embodiments, the methacryloyl-substituted, dopylated gelatin hydrogel has a degree of dopylation between 5% and 15%, or 10%. In some embodiments, the methacryloyl-substituted, dopylated gelatin hydrogel is present at a concentration between 5% and 25% (w/v), 10% and 20% (w/v), or 15% (w/v). In some embodiments, the tissue adhesive has a burst pressure of ≥5 kPa or ≥7 kPa. In some embodiments, the tissue adhesive has a wound closure strength of ≥100 kPa or ≥110 kPa. In some embodiments, the tissue adhesive has a shear resistance strength of ≥600 kPa or ≥800 kPa.

Certain aspects of the present invention are directed to a method for adhering or sealing soft tissue, comprising the steps of:
  a) Applying a composition comprising a light activated methacryloyl-substituted gelatin, a photoinitiator and a pharmaceutically acceptable carrier to the soft tissue to be adhered or sealed; and
  b) Exposing the composition to UV or visible light.

In some embodiments, the soft tissue is a highly stressed elastic tissue. In some embodiments, the soft tissue is selected from the group consisting of lung, cardiovascular, skin, kidney, bladder, urethra, dura mater, liver, gastrointestinal, etc. In some embodiments, the method provides a seal against leakage of a fluid through the soft tissue. Preferably, the fluid is selected from the group consisting of air, blood, water, urine, lymph, cerebral spinal fluid, bile, gastrointestinal contents, etc. In some embodiments, the seal against leakage lasts in vivo for at least 7 days, at least 14 days, at least 21 days, or at least 28 days. In some embodiments, the composition is exposed to UV light for a time period between 30 seconds and 6 minutes, between 1 minute and 5 minutes, between 2 minutes and 4 minutes, or 3 minutes. In some embodiments, the methacryloyl-substituted gelatin has a degree of methacryloyl substitution between 50% and 90%, 60% and 85%, or 70% and 80%. In some embodiments, the methacryloyl-substituted gelatin is present at a concentration between 10% and 40% (w/v), 15% and 35% (w/v), 20% and 30% (w/v), or 25% (w/v). In some embodiments, the photoinitiator is selected from the group consisting of 1-[4-(2-hydroxyethoxy)-phenyl]-2-hydroxy-2-methyl-1-propane-1-one, azobisisobutyronitrile, benzoyl peroxide, di-tert-butyl peroxide, 2,2-dimethoxy-2-phenylacetophenone, Eosin Y, etc. In some embodiments, the pharmaceutically acceptable carrier is selected from the group consisting of phosphate-buffered saline, water, etc. In some embodiments, the composition further comprises a hemostatic agent selected from the group consisting of blood coagulation factors, prothrombin, thrombin, silicate nanoparticles, etc. In some embodiments, the composition further comprises an antibacterial agent selected from the group consisting of silver nanoparticles, copper oxide nanoparticles, nanoparticle-carried antibiotic drugs, penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim sulfamethoxazole, chitosan, etc. In some embodiments, the method does not comprise suturing or stapling the soft tissue to be adhered or sealed.

In some embodiments of the method for adhering or sealing soft tissue, the methacryloyl-substituted gelatin further comprises dopamine conjugated to the gelatin. In some embodiments, the methacryloyl-substituted, dopylated gelatin has a degree of dopylation between 5% and 15%, or 10%. In some embodiments, the methacryloyl-substituted, dopylated gelatin is present at a concentration between 5% and 25% (w/v), 10% and 20% (w/v), or 15% (w/v). In some embodiments, the photoinitiator is Eosin Y and the composition is exposed to visible light for a time period within 10-60 seconds.

BRIEF DESCRIPTION OF THE DRAWINGS

The patent or application file contains at least on drawing executed in color. Copies of this patent or patent application publication with color drawings(s) will be provided by the Office upon request and payment of the necessary fee.

FIG. 3 depicts ASTM standard lap-shear tests of GelSEAL hydrogels produced according to Examples 1-3. Schematic displaying GelSEAL tissue adhesive application on gelatin-coated glass slides (a.i), UV-triggered crosslinking between the glass slides (a.ii) and subsequent tensile testing (a.iii). Comparative testing revealed a crosslinking time of 3 min (b) and a GelSEAL concentration of 25% (c) to yield the best lap shear results, which were improved as compared to Coseal™ and Evicel®. *p<0.05; p<0.01; *p<0.001.

FIG. 10 depicts a) a schematic of the modified standard test method for strength properties of tissue adhesives in lap-shear by tension loading (ASTM F2255-05); and b) Adhesive strength of GelMA-Dopamine and GelMA (produced according to Examples 6 and 7) compared to CoSeal, Evicel, and Progel.

DETAILED DESCRIPTION

Figure 1A:
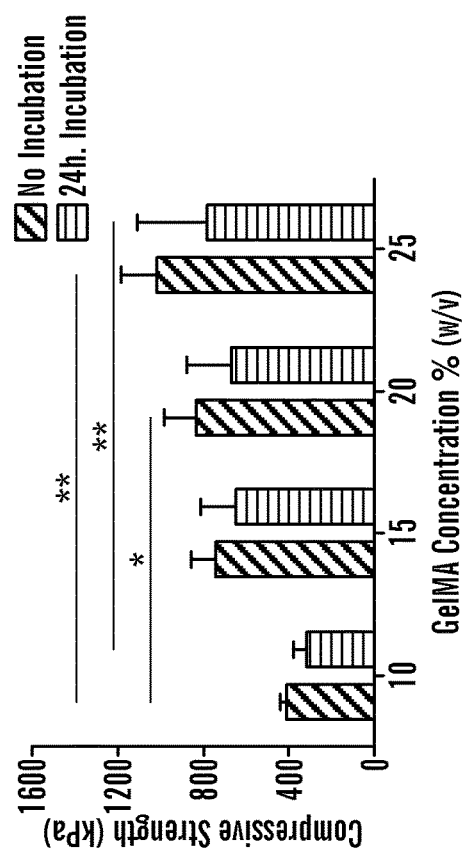
FIG. 1 depicts concentration-dependent mechanical characteristics of GelSEAL hydrogels produced according to Examples 1 and 2. Representative stress-strain curves show higher compressive stiffness at higher GelMA concentrations (a), and the compressive strength increased significantly (b), whereas 24 h incubation of the crosslinked hydrogel in PBS did not reduce the performance. Tensile testing revealed enhanced tensile stiffness (c, representative curves) and increased tensile strength (d) at higher GelMA concentrations. On the contrary, the swelling ratio was significantly lower at higher GelMA concentrations, independently on the time point after crosslinking (e). Scanning electron micrsoscope imaging of a 25% (w/v) GelMA cross section (f). Percentages in (e) represent GelMA concentrations; scale bar, 50 µm (20 µm in the small picture); *p<0.05; p<0.01; *p<0.001; ****p<0.0001.

Certain aspects of the present invention are directed to a biocompatible and photocrosslinkable gelatin-based tissue adhesive or sealant comprising methacryloyl-substituted gelatin (GelMA), having superior material properties to tissue adhesives currently available on the commercial market for clinical applications. As used herein, "methacryloyl-substituted gelatin" is defined as gelatin having free amines and/or free hydroxyls that have been substituted with at least one methacrylamide group and/or at least one methacrylate group. GelMA comprises modified natural extracellular matrix components that can be crosslinked via UV exposure to create an elastic and biodegradable hydrogel (GelSEAL). Natural extracellular matrix components may include gelatin derived from animals including, but not limited to, pig, cow, horse, chicken, fish, etc. Advantageously, the gelatin can be harvested under sterile conditions from animals in pathogen-free barrier facilities to eliminate the risk of transmission of disease (e.g, hepatitis C, human immunodeficiency virus, etc.)

In situ photopolymerization of GelMA facilitates easy delivery even to technically demanding locations, as e.g., during minimally invasive surgery, and allows for curing of the sealant exactly according to the required geometry of the tissue to be sealed, which is an advantage over pre-formed materials, as e.g., hemostyptic collagen or fibrinogen/thrombin scaffolds. Besides physical interconnection of the curing sealant with the tissue surface, gelatin offers additional options to interact with tissues in defect areas. Since gelatin contains multiple domains that bind to cell-surface receptors and extracellular matrix proteins, initial connection of the sealant to the tissue as well as subsequent cell attachment to and cell growth on the sealant are promoted. In some embodiments, the gelatin may be functionalized with anchoring integrins (e.g., lymphocyte function-associated antigen-1 or macrophage-1 molecule, which bind to the surface protein intercellular adhesion molecule-1 expressed on mesothelial cells that cover the lung surface.

Gelatin comprises amino acids, some of which have side chains that terminate in amines (e.g., lysine, arginine, asparagine, glutamine). One or more of these terminal amines can be substituted with methacryloyl groups to produce methacryloyl-substituted gelatin. In some embodiments, with exposure to UV or visible light in the presence of a photoinitiator, the methacryloyl groups on one gelatin molecule can react with the methacryloyl groups on another gelatin molecule to crosslink the methacryloyl-substituted gelatin and produce a hydrogel. In some embodiments, the gelatin may be functionalized with methacryloyl groups by reacting gelatin with suitable reagents including, but not limited to, methacrylic anhydride, methacryloyl chloride, etc.

Certain exemplary embodiments of the tissue adhesive of the present invention comprise a photoinitiator. "Photoinitiator" as used herein refers to any chemical compound that decomposes into free radicals when exposed to light. Preferably, the photoinitiator produces free radicals when exposed to ultraviolet (UV) or visible light. Examples of photoinitiators include, but are not limited to, 1-[4-(2-hydroxyethoxy)-phenyl]-2-hydroxy-2-methyl-1-propane-1-one (Irgacure 2959, BASF, Florham Park, N.J., USA), azobisisobutyronitrile, benzoyl peroxide, di-tert-butyl peroxide, 2,2-dimethoxy-2-phenylacetophenone, Eosin Y, etc. In some embodiments, the photoinitiator is 1-[4-(2-hydroxyethoxy)-phenyl]-2-hydroxy-2-methyl-1-propane-1-one. In some embodiments, the photoinitiator is Eosin Y.

The mechanical properties of GelSEAL can be tuned for various applications by changing the degree of methacryloyl substitution, methacryloyl-substituted gelatin concentration and light exposure time. As used herein, the degree of methacryloyl substitution is defined as the percentage of free amines or hydroxyls in the gelatin that have been substituted with methacryloyl groups. In some embodiments, methacryloyl-substituted gelatin has a degree of methacryloyl substitution between 20% and 90%, 50% and 90%, 60% and 85%, 65% and 75%, or 70 and 80%. As used herein, the concentration of methacryloyl-substituted gelatin is defined as the weight of methacryloyl-substituted gelatin divided by the volume of solvent (w/v), expressed as a percentage. In some embodiments, the methacryloyl-substituted gelatin is present at a concentration between 10% and 40% (w/v), 15% and 35% (w/v), 20% and 30% (w/v), or about 5%, 10%, 15%, 20%, or 25% (w/v). The solvent may be a pharmaceutically acceptable carrier. In some embodiments, the methacryloyl-substituted gelatin has a combination of any of the above degrees of methacryloyl substitution and any of the above concentrations, e.g., a degree of methacryloyl substitution between 50% and 90% and a concentration between 10% and 40% (w/v), a degree of methacryloyl substitution between 60% and 85% and a concentration between 20% and 30% (w/v), a degree of methacryloyl substitution between 70% and 80% and a concentration of 25% (w/v).

Certain exemplary embodiments of the present invention comprise a pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation and is compatible with administration to a subject, for example a human. It must also be suitable for use in contact with any tissues or organs with which it may come in contact, meaning that it must not carry a risk of toxicity, irritation, allergic response, immunogenicity, or any other complication that excessively outweighs its therapeutic benefits. Examples of pharmaceutically acceptable carriers include, but are not limited to, a solvent or dispersing medium containing, for example, water, pH buffered solutions (e.g., phosphate buffered saline (PBS), HEPES, TES, MOPS, etc.), isotonic saline, Ringer's solution, polyol (for example, glycerol, propylene glycol, liquid polyethylene glycol, and the like), alginic acid, ethyl alcohol, and suitable mixtures thereof. In some embodiments, the pharmaceutically acceptable carrier can be a pH buffered solution (e.g. PBS).

Certain exemplary embodiments of the present invention comprise a hemostatic agent. A "hemostatic agent" is defined herein as any substance that promotes hemostasis (i.e., stops bleeding). Evaluation of the hemostatic potential of various embodiments of the present invention can be performed in the liver laceration model, which has been recently used to test the effect of shear-thinning nanocomposite hydrogels when applied in otherwise lethal hemorrhage [GAHARWAR]. Some embodiments include platelet-like nanoparticles (e.g., silicate nanoparticles), which may create an effective sealant with strong hemostatic properties [ANSELMO]. Some embodiments include active biological components such as blood coagulation factors (e.g., thrombin, prothrombin, etc.) which can participate in blood clotting.

Many soft tissue surgeries are performed on tissues that contact a non-sterile environment (e.g., pulmonary airways, gastrointestinal tract, etc.), and are susceptible to severe infections after surgery. Thus, certain exemplary embodiments of tissue adhesive or sealant of the present invention comprise an antibacterial agent. The term "antibacterial agent" is used herein to describe a compound or composition which decreases the viability of a microorganism, or which inhibits the growth or reproduction of a microorganism. Exemplary antibacterial agents include, but are not limited to, silver nanoparticles, copper oxide nanoparticles, nanoparticle-carried antibiotic drugs [BUCKLEY, DEACON, HASSAN, NAN], penicillins, cephalosporins, penems, carbapenems, monobactams, aminoglycosides, sulfonamides, macrolides, tetracycline, lincosides, quinolones, chloramphenicol, vancomycin, metronidazole, rifampin, isoniazid, spectinomycin, trimethoprim, sulfamethoxazole, chitosan, and the like. Other agents include, without limitation, antifouling or biocidal, bacteriostatic or bactericidal agents, or other antibacterial agents.

Certain aspects of the present invention are directed to a tissue adhesive or sealant comprising a crosslinked methacryloyl-substituted gelatin hydrogel and a pharmaceutically acceptable carrier. As used herein, a "hydrogel" is a network of hydrophilic polymer chains forming a colloidal gel. In some embodiments, the crosslinked methacryloyl-substituted gelatin hydrogel has a degree of methacryloyl substitution between 20% and 90%, 40% and 90%, 60% and 85%, 65% and 75%, or 70% and 80%. In some embodiments, the crosslinked methacryloyl-substituted gelatin hydrogel is present at a concentration between 10% and 40% (w/v), 15% and 35% (w/v), 20% and 30% (w/v), or about 5%, 10%, 15%, 20%, or 25% (w/v) in the pharmaceutically acceptable carrier. In some embodiments, the crosslinked methacryloyl-substituted gelatin hydrogel has a combination of any of the above degrees of methacryloyl substitution and any of the above concentrations. In some embodiments, the crosslinked methacryloyl-substituted gelatin hydrogel has a degree of methacryloyl substitution between 60% and 80% and a concentration between 10% and 40% (w/v) in the pharmaceutically acceptable carrier, a degree of methacryloyl substitution between 65% and 75% and a concentration between 20% and 30% (w/v), or a degree of methacryloyl substitution between 68% and 72% and a concentration of 25% (w/v).

In one embodiment, the tissue adhesive of the present invention performed better than the two commercially available surgical glues, Evicel® (a fibrin-based sealant) and Coseal™ (a polyethylene glycol (PEG)-based sealant), for all of the studied adhesion tests. These tests include the Lap Shear test (ASTM F2255-05), the Wound Closure test (ASTM F2458-05), and the Burst Pressure test (ASTM F2392-04). In one embodiment, a tissue adhesive of the present invention comprising crosslinked methacryloyl-substituted gelatin hydrogel produced from a GelMA concentration of 25% (w/v) attained an adhesion strength of 49±9 kPa during the Wound Closure test as compared to the 19±17 kPa and 26±5 kPa of Evicel and Coseal, respectively. In addition, based on the Lap Shear test, this embodiment showed a shear strength of 262±55 kPa as opposed to just 207±67 kPa and 70±21 kPa attained by Evicel and Coseal, respectively. This embodiment also out-performed both commercial glues in the Burst Pressure test, reaching a burst pressure of 2.17±0.83 psi in comparison to 0.22±0.14 psi of Evicel and 0.24±0.02 psi of Coseal. In some embodiments, the tissue adhesive has a wound closure strength of ≥20 kPa, ≥40 kPa, or ≥50 kPa. In some embodiments, the tissue adhesive has a shear resistance strength of ≥200 kPa, ≥250 kPa, or ≥300 kPa. In some embodiments, the tissue adhesive has a burst pressure of ≥5 kPa, ≥10 kPa, or ≥15 kPa.

Certain aspects of the present invention are directed to a method for adhering or sealing soft tissue, comprising the steps of:
a) Applying a composition comprising a light activated methacryloyl-substituted gelatin, a photoinitiator and a pharmaceutically acceptable carrier to the soft tissue to be adhered or sealed; and
b) Exposing the composition to UV or visible light.

In some embodiments, the method of the present invention can be used to adhere or seal various soft tissues such as lung, cardiovascular, skin, kidney, bladder, urethra, dura mater, liver, gastrointestinal, etc. In some embodiments, the method is particularly useful for adhering or sealing soft tissue that is highly stressed elastic tissue. As used herein, "highly stressed elastic tissue" is defined as any tissue that reversibly deforms under repeated stress, strain, shear, pressure, or other mechanical forces in vivo. Advantageously, the method of the present invention produces a tissue adhesive having high elasticity and adhesion strength. Thus, some embodiments of the method do not comprise the use of additional closure methods such as staples or sutures to adhere or seal the soft tissue.

In some embodiments, the method provides a seal against leakage of a fluid through the soft tissue. Preferably, the fluid is selected from the group consisting of air, blood, water, urine, lymph, cerebral spinal fluid, bile, gastrointestinal contents, etc. Gastrointestinal contents include any fluid in the gastrointestinal tract (e.g., digested food, digestive juices, gastric acid, pancreatic secretions, bile, etc.) As used herein, a seal against leakage means that fluid does not pass through or around the tissue adhesive or sealant where it is applied to the soft tissue. In some embodiments, the seal against leakage lasts in vivo for at least 7 days, at least 14 days, at least 21 days, or at least 28 days. In some embodiments, the seal against leakage lasts until the tissue defect is healed.

The mechanical properties of GelSEAL can be tuned for various applications by changing the UV or visible light exposure time. Without being bound by theory, longer UV or visible light exposure time produces more crosslinkage in the methacryloyl-substituted gelatin, providing a hydrogel with improved mechanical properties, such as adhesion strength, shear strength, compressive strength, tensile strength, etc. In some embodiments, the composition is exposed to UV or visible light for a time period between 30 seconds and 6 minutes, between 1 minute and 5 minutes, between 2 minutes and 4 minutes, or 3 minutes. In some embodiments, the composition is exposed to UV or visible light for a time period of less than one minute, within 10-60 seconds, 15-45 seconds, 20 seconds, or 30 seconds. In some embodiments, a composition comprising a light activated methacryloyl-substituted gelatin, 1-[4-(2-hydroxyethoxy)-phenyl]-2-hydroxy-2-methyl-1-propane-1-one as the photoinitiator, and a pharmaceutically acceptable carrier is exposed to UV light for about 3 minutes.

In certain embodiments of the tissue adhesives and methods disclosed herein, the methacryloyl-substituted gelatin further comprises dopamine conjugated to the gelatin. Gelatin comprises amino acids, some of which have side chains that terminate in carboxylic acids or amides (e.g., aspartic acid, glutamic acid, asparagine, glutamine). One or more of these terminal carbonyls can be substituted with dopamine to produce dopylated gelatin. As used herein, "dopylated gelatin" is defined as gelatin having terminal carboxylic acids or amides that have been substituted with at least one dopamine group. Dopylated gelatin can be further substituted with methacryloyl groups as described herein to produce methacryloyl-substituted, dopylated gelatin. As used herein, the degree of dopylation is defined as the percentage of terminal carbonyls in the gelatin that have been substituted with dopamine groups. In some embodiments, the methacryloyl-substituted, dopylated gelatin has a degree of dopylation between 5% and 15%, or 10%. As used herein, the concentration of methacryloyl-substituted, dopylated gelatin is defined as the weight of methacryloyl-substituted, dopylated gelatin divided by the volume of solvent (w/v), expressed as a percentage. In some embodiments, the methacryloyl-substituted, dopylated gelatin is present at a concentration between 5% and 25% (w/v), 10% and 20% (w/v), or 15% (w/v).

In certain embodiments of the tissue adhesives and methods disclosed herein, the methacryloyl-substituted, dopylated gelatin can be photo-crosslinked into a hydrogel with any photoinitiator and UV or visible light for any time period as described herein. Preferably, the photoinitiator is Eosin Y and the methacryloyl-substituted, dopylated gelatin is exposed to visible light for a time period within 10-60 seconds.

Advantageously, a tissue adhesive comprising methacryloyl-substituted, dopylated gelatin hydrogel has improved mechanical properties over commercially available surgical adhesives, such as Progel, CoSeal, and Evicel. In some embodiments, the tissue adhesive has a burst pressure of ≥5 kPa or ≥7 kPa. In some embodiments, the tissue adhesive has a wound closure strength of ≥100 kPa or ≥110 kPa. In some embodiments, the tissue adhesive has a shear resistance strength of ≥600 kPa or ≥800 kPa.

Aspects of the invention disclosed herein can be illustrated by any of the following numbered paragraphs:

1. A tissue adhesive comprising a light activated methacryloyl-substituted gelatin, a photoinitiator and a pharmaceutically acceptable carrier.
2. The tissue adhesive of paragraph 1, wherein the methacryloyl-substituted gelatin has a degree of methacryloyl substitution between 50% and 90%.
3. The tissue adhesive of paragraph 1 or 2, wherein the methacryloyl-substituted gelatin has a degree of methacryloyl substitution between 60% and 85%.
4. The tissue adhesive of any one of paragraphs 1-3, wherein the methacryloyl-substituted gelatin has a degree of methacryloyl substitution between 70% and 80%.
5. The tissue adhesive of any one of paragraphs 1-4, wherein the methacryloyl-substituted gelatin is present at a concentration between 10% and 40% (w/v).
6. The tissue adhesive of any one of paragraphs 1-5, wherein the methacryloyl-substituted gelatin is present at a concentration between 15% and 35% (w/v).
7. The tissue adhesive of any one of paragraphs 1-6, wherein the methacryloyl-substituted gelatin is present at a concentration between 20% and 30% (w/v).
8. The tissue adhesive of any one of paragraphs 1-7, wherein the methacryloyl-substituted gelatin is present at a concentration of 25% (w/v).
9. The tissue adhesive of any one of paragraphs 1-8, wherein the photoinitiator is selected from the group consisting of: 1-[4-(2-hydroxyethoxy)-phenyl]-2-hydroxy-2-methyl-1-propane-1-one, azobisisobutyronitrile, benzoyl peroxide, di-tert-butyl peroxide, 2,2-dimethoxy-2-phenylacetophenone, Eosin Y, and any combination thereof.
10. The tissue adhesive of any one of paragraphs 1-9, wherein the pharmaceutically acceptable carrier is phosphate-buffered saline or water.
11. The tissue adhesive of any one of paragraphs 1-10, further comprising a hemostatic agent selected from the group consisting of blood coagulation factors, prothrombin, thrombin, silicate nanoparticles, and any combination thereof.
12. The tissue adhesive of any one of paragraphs 1-11, further comprising an antibacterial agent selected from the group consisting of silver nanoparticles, copper oxide nanoparticles, nanoparticle-carried antibiotic drugs, penicillins, cephalosporins, penems, carbapenems, monobactams, aminoglycosides, sulfonamides, macrolides, tetracycline, lincosides, quinolones, chloramphenicol, vancomycin, metronidazole, rifampin, isoniazid, spectinomycin, trimethoprim sulfamethoxazole, chitosan, and any combination thereof.
13. A tissue adhesive comprising a crosslinked methacryloyl-substituted gelatin hydrogel and a pharmaceutically acceptable carrier, wherein the crosslinked methacryloyl-substituted gelatin hydrogel has a degree of methacryloyl substitution between 50% and 90% and a concentration between 10% and 40% (w/v) in the pharmaceutically acceptable carrier.
14. The tissue adhesive of paragraph 13, wherein the crosslinked methacryloyl-substituted gelatin hydrogel has a degree of methacryloyl substitution between 60% and 85% and a concentration between 20% and 30% (w/v).
15. The tissue adhesive of paragraph 13 or 14, wherein the crosslinked methacryloyl-substituted gelatin hydrogel has a degree of methacryloyl substitution between 70% and 80% and a concentration of 25% (w/v).

16. The tissue adhesive of any one of paragraphs 13-15, having a wound closure strength of ≥20 kPa.
17. The tissue adhesive of any one of paragraphs 13-16, having a wound closure strength of ≥40 kPa.
18. The tissue adhesive of any one of paragraphs 13-17, having a wound closure strength of ≥50 kPa.
19. The tissue adhesive of any one of paragraphs 13-18, having a shear resistance strength of ≥200 kPa.
20. The tissue adhesive of any one of paragraphs 13-19, having a shear resistance strength of ≥250 kPa.
21. The tissue adhesive of any one of paragraphs 13-20, having a shear resistance strength of ≥300 kPa.
22. The tissue adhesive of any one of paragraphs 13-21, having a burst pressure of ≥5 kPa.
23. The tissue adhesive of any one of paragraphs 13-22, having a burst pressure of ≥10 kPa.
24. The tissue adhesive of any one of paragraphs 13-23, having a burst pressure of ≥15 kPa.
25. The tissue adhesive of any one of paragraphs 13-24, further comprising a hemostatic agent selected from the group consisting of blood coagulation factors, prothrombin, thrombin, silicate nanoparticles, and any combination thereof.
26. The tissue adhesive of any one of paragraphs 13-25, further comprising an antibacterial agent selected from the group consisting of silver nanoparticles, copper oxide nanoparticles, nanoparticle-carried antibiotic drugs, penicillins, cephalosporins, penems, carbapenems, monobactams, aminoglycosides, sulfonamides, macrolides, tetracycline, lincosides, quinolones, chloramphenicol, vancomycin, metronidazole, rifampin, isoniazid, spectinomycin, trimethoprim, sulfamethoxazole, chitosan, and any combination thereof.
27. A method for adhering or sealing soft tissue, comprising the steps of:
    a) Applying a composition comprising a light activated methacryloyl-substituted gelatin, a photoinitiator and a pharmaceutically acceptable carrier to the soft tissue to be adhered or sealed; and
    b) Exposing the composition to UV or visible light.
28. The method of paragraph 27, wherein the soft tissue is a highly stressed elastic tissue.
29. The method of paragraph 27 or 28, wherein the soft tissue is selected from the group consisting of: lung, cardiovascular, skin, kidney, bladder, urethra, dura mater, liver, and gastrointestinal tissues.
30. The method of any one of paragraphs 27-29, wherein the method provides a seal against leakage of a fluid through the soft tissue.
31. The method of any one of paragraphs 27-30, wherein the fluid is selected from the group consisting of air, blood, water, urine, lymph, cerebral spinal fluid, bile and gastrointestinal contents.
32. The method of any one of paragraphs 27-31, wherein the seal against leakage lasts in vivo for at least 7 days.
33. The method of any one of paragraphs 27-32, wherein the seal against leakage lasts in vivo for at least 14 days.
34. The method of any one of paragraphs 27-33, wherein the seal against leakage lasts in vivo for at least 21 days.
35. The method of any one of paragraphs 27-34, wherein the seal against leakage lasts in vivo for at least 28 days.
36. The method of any one of paragraphs 27-35, wherein the composition is exposed to UV or visible light for a time period between 1 minute and 5 minutes.
37. The method of any one of paragraphs 27-36, wherein the composition is exposed to UV or visible light for a time period between 2 minutes and 4 minutes.
38. The method of any one of paragraphs 27-37, wherein the composition is exposed to UV or visible light for a time period of 3 minutes.
39. The method of any one of paragraphs 27-35, wherein the composition is exposed to UV or visible light for a time period within 10-60 seconds.
40. The method of any one of paragraphs 27-39, wherein the methacryloyl-substituted gelatin has a degree of methacryloyl substitution between 50% and 90%.
41. The method of any one of paragraphs 27-40, wherein the methacryloyl-substituted gelatin has a degree of methacryloyl substitution between 60% and 85%.
42. The method of any one of paragraphs 27-41, wherein the methacryloyl-substituted gelatin has a degree of methacryloyl substitution between 70% and 80%.
43. The method of any one of paragraphs 27-42, wherein the methacryloyl-substituted gelatin is present at a concentration between 10% and 40% (w/v).
44. The method of any one of paragraphs 27-43, wherein the methacryloyl-substituted gelatin is present at a concentration between 15% and 35% (w/v).
45. The method of any one of paragraphs 27-44, wherein the methacryloyl-substituted gelatin is present at a concentration between 20% and 30% (w/v).
46. The method of any one of paragraphs 27-45, wherein the methacryloyl-substituted gelatin is present at a concentration of 25% (w/v).
47. The method of any one of paragraphs 27-46, wherein the photoinitiator is selected from the group consisting of: 1-[4-(2-hydroxyethoxy)-phenyl]-2-hydroxy-2-methyl-1-propane-1-one, azobisisobutyronitrile, benzoyl peroxide, di-tert-butyl peroxide, 2,2-dimethoxy-2-phenylacetophenone, Eosin Y, and any combination thereof.
48. The method of any one of paragraphs 27-47, wherein the pharmaceutically acceptable carrier is phosphate-buffered saline, or water.
49. The method of any one of paragraphs 27-48, wherein the composition further comprises a hemostatic agent selected from the group consisting of blood coagulation factors, prothrombin, thrombin, silicate nanoparticles, and any combination thereof.
50. The method of any one of paragraphs 27-49, wherein the composition further comprises an antibacterial agent selected from the group consisting of silver nanoparticles, copper oxide nanoparticles, nanoparticle-carried antibiotic drugs, penicillins, cephalosporins, penems, carbapenems, monobactams, aminoglycosides, sulfonamides, macrolides, tetracycline, lincosides, quinolones, chloramphenicol, vancomycin, metronidazole, rifampin, isoniazid, spectinomycin, trimethoprim, sulfamethoxazole, chitosan, and any combination thereof.
51. The method of any one of paragraphs 27-50, wherein the method does not comprise suturing or stapling the soft tissue to be adhered or sealed.
52. The tissue adhesive of any one of paragraphs 1-12, wherein the methacryloyl-substituted gelatin further comprises dopamine conjugated to the gelatin.
53. The tissue adhesive of paragraph 52, wherein methacryloyl-substituted, dopylated gelatin has a degree of dopylation between 5% and 15%.
54. The tissue adhesive of paragraph 52 or 53, wherein the methacryloyl-substituted, dopylated gelatin has a degree of dopylation of 10%.
55. The tissue adhesive of any one of paragraphs 52-54, wherein the methacryloyl-substituted, dopylated gelatin is present at a concentration between 5% and 25% (w/v).

56. The tissue adhesive of any one of paragraph 52-55, wherein the methacryloyl-substituted, dopylated gelatin is present at a concentration between 10% and 20% (w/v).
57. The tissue adhesive of any one of paragraphs 52-56, wherein the methacryloyl-substituted, dopylated gelatin is present at a concentration of 15% (w/v).
58. The tissue adhesive of any one of paragraphs 13-26, wherein the methacryloyl-substituted gelatin hydrogel further comprises dopamine conjugated to the gelatin.
59. The tissue adhesive of paragraph 58, wherein methacryloyl-substituted, dopylated gelatin hydrogel has a degree of dopylation between 5% and 15%.
60. The tissue adhesive of paragraph 58 or 59, wherein the methacryloyl-substituted, dopylated gelatin hydrogel has a degree of dopylation of 10%.
61. The tissue adhesive of any one of paragraphs 58-60, wherein the methacryloyl-substituted, dopylated gelatin hydrogel is present at a concentration between 5% and 25% (w/v).
62. The tissue adhesive of any one of paragraphs 58-61, wherein the methacryloyl-substituted, dopylated gelatin hydrogel is present at a concentration between 10% and 20% (w/v).
63. The tissue adhesive of any one of paragraphs 58-62, wherein the methacryloyl-substituted, dopylated gelatin hydrogel is present at a concentration of 15% (w/v).
64. The tissue adhesive of any one of paragraphs 58-63, having a burst pressure of ≥5 kPa.
65. The tissue adhesive of any one of paragraphs 58-64, having a burst pressure of ≥7 kPa.
66. The tissue adhesive of any one of paragraphs 58-65, having a wound closure strength of ≥110 kPa.
67. The tissue adhesive of any one of paragraphs 58-66, having a shear resistance strength of ≥600 kPa.
68. The tissue adhesive of any one of paragraphs 58-67, having a shear resistance strength of ≥800 kPa.
69. The method of any one of paragraphs 27-51, wherein the methacryloyl-substituted gelatin further comprises dopamine conjugated to the gelatin.
70. The method of paragraph 69, wherein methacryloyl-substituted, dopylated gelatin has a degree of dopylation between 5% and 15%.
71. The method of paragraph 69 or 70, wherein the methacryloyl-substituted, dopylated gelatin has a degree of dopylation of 10%.
72. The method of any one of paragraphs 69-71, wherein the methacryloyl-substituted, dopylated gelatin is present at a concentration between 5% and 25% (w/v).
73. The method of any one of paragraphs 69-72, wherein the methacryloyl-substituted, dopylated gelatin is present at a concentration between 10% and 20% (w/v).
74. The method of any one of paragraphs 69-73, wherein the methacryloyl-substituted, dopylated gelatin is present at a concentration of 15% (w/v).
75. The method of any one of paragraphs 69-74, wherein the photoinitiator is Eosin Y and the composition is exposed to visible light for a time period within 10-60 seconds.

Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Other than in the operating examples, or where otherwise indicated, all numbers expressing quantities of ingredients or reaction conditions used herein should be understood as modified in all instances by the term "about." The term "about" when used to described the present invention, in connection with percentages means ±1%, ±1.5%, ±2%, ±2.5%, ±3%, ±3.5%, ±4%, ±4.5%, or ±5%.

The singular terms "a," "an," and "the" include plural referents unless context clearly indicates otherwise. Similarly, the word "or" is intended to include "and" unless the context clearly indicates otherwise.

As used herein the terms "comprising" or "comprises" means "including" or "includes" and are used in reference to compositions, methods, systems, and respective component(s) thereof, that are useful to the invention, yet open to the inclusion of unspecified elements, whether useful or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, systems, and respective components thereof as described herein, which are exclusive of any element not recited in that description of the embodiment.

The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

One skilled in the art would also readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

EXAMPLES

The disclosure is further illustrated by the following examples which should not be construed as limiting. The examples are illustrative only, and are not intended to limit, in any manner, any of the aspects described herein. The following examples do not in any way limit the invention.

The suitability of GelMA hydrogels as tissue adhesives was studied, in particular as sealants (GelSEAL) for highly stressed elastic tissue, as e.g. lung parenchyma. Therefore, ASTM (American Society for Testing and Materials) standard tests for adhesive properties were conducted, comparing GelSEAL to clinically available fibrin-based (e.g. Evicel®) and poly(ethylene glycol)-based (e.g. CoSeal™) glues. Furthermore, the actual biocompatibility and the in vivo performance in sealing lung leakages were analyzed in rat implantation models.

Histology and Immunohistology

Histology and immunohistology of GelSEAL was conducted on paraformaldehyde-fixed 6 μm cryo-sections of the explants as previously reported [ASSMANN]. Hematoxylin/eosin staining was performed to obtain microscopic overview. For immunohistology, the primary antibodies anti-CD3 and anti-CD68 (Abcam, Cambridge, Mass., USA), and Alexa Fluor®-conjugated secondary antibodies (Life Technologies, Carlsbad, Calif., USA) were used. Sections were covered with DAPI-containing Vectashield mounting medium (Vector Labs, Peterborough, United Kingdom) and visualized on an Axio Observer microscope (Zeiss, Jena, Germany).

Statistics

Continuous variables are displayed as mean values±standard deviations. Group comparisons were conducted by one-way-ANOVA with Bonferroni post-hoc tests. P-values <0.05 were assumed to indicate significance. Data analysis was conducted with GraphPad Prism (GraphPad Software, La Jolla, Calif., USA).

Example 1: Synthesis of Methacryloyl-Substituted Gelatin (GelMA)

GelMA was synthesized as previously described [NICHOL]. In brief, 10% (w/v) porcine gelatin (Sigma-Aldrich, St. Louis, Mo., USA) was dissolved in phosphate-buffered saline (PBS) and heated at 60° C. for 20 minutes. Dropwise addition of 8% (v/v) methacrylic anhydride (Sigma-Aldrich, St. Louis, Mo., USA) under continuous stirring at 50° C. for 3 hours was followed by dilution with PBS and dialysis against deionized water at 40-50° C. for 7 days. After sterile filtration and lyophilization for 4 days, GelMA was stored at −80° C. until experimental use.

Example 2: Preparation and Material Characterization of GelMA Hydrogels

Freeze-dried GelMA produced according to Example 1 was dissolved in PBS at concentrations of 10, 15, 20 or 25% (w/v). After addition of 0.5% (w/v) 1-[4-(2-Hydroxyethoxy)-phenyl]-2-hydroxy-2-methyl-1-propane-1-one (Irgacure 2959, BASF, Florham Park, N.J., USA) as photoinitiator and dissolving at 80° C., the prepolymer solutions were photocrosslinked to hydrogels (GelSEAL) by UV light irradiation (Omnicure S2000, 320-500 nm filter, EXFO Photonic Solutions Inc., Quebec, Canada).

For visualizing porosity, circular GelSEAL hydrogel samples (5 mm in diameter) were fabricated, freeze-dried, sputter-coated with gold and imaged on a scanning electron microscope (FEI/Philips XL30 FEG SEM).

Mechanical testing of GelSEAL samples was conducted as previously published [NICHOL]. Briefly, prepolymer solution was photocrosslinked to produce the following geometries: discs for compressive testing (n=3 to 5; 6 mm in diameter and 1.5 mm in height) and cuboids for tensile testing (n=7 to 10; 3 mm in width, 14 mm in length and 1.5 mm in thickness). The hydrogels were either directly analyzed or stored in PBS at 4° C. for 24 hours before being examined on an mechanical testing system 5542 (Instron, Norwood, Mass., USA). The strain rate was set to 1 mm/min for compressive testing and tensile testing. The compressive strength and the ultimate tensile strength of the samples were determined at the point of breaking or tearing of the hydrogels.

In order to analyze the swelling characteristics, GelSEAL hydrogel samples (n=5) were allowed to swell in PBS for 1, 2 or 3 days. At the end of the experiment, excess liquid was gently removed with a tissue, and the wet weight was measured. After lyophilization, the dry weight of the samples was measured, and the swelling ratio was calculated as (wet weight-dry weight)/dry weight.

Concentration-Dependent Material Characteristics of GelSEAL

Figure 1C:
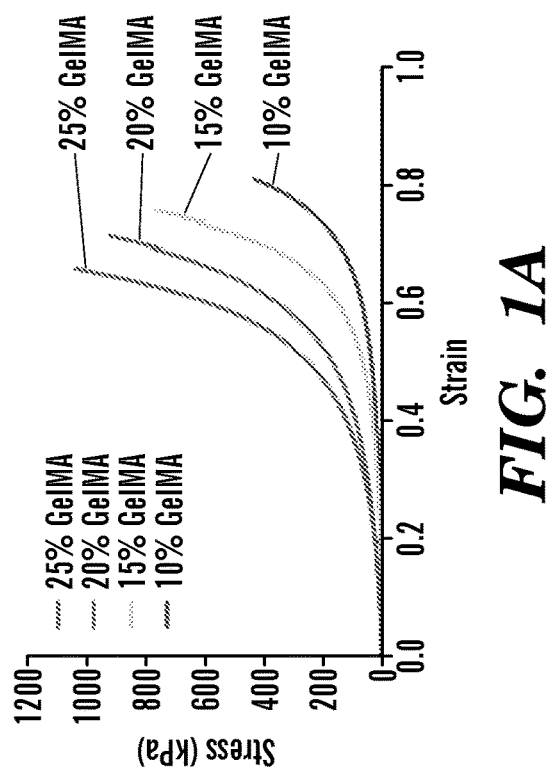
Figure 1B:
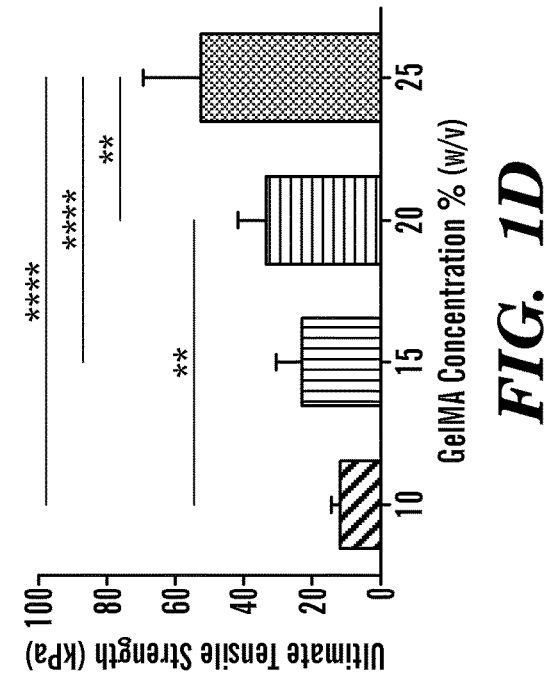
Figure 1D:
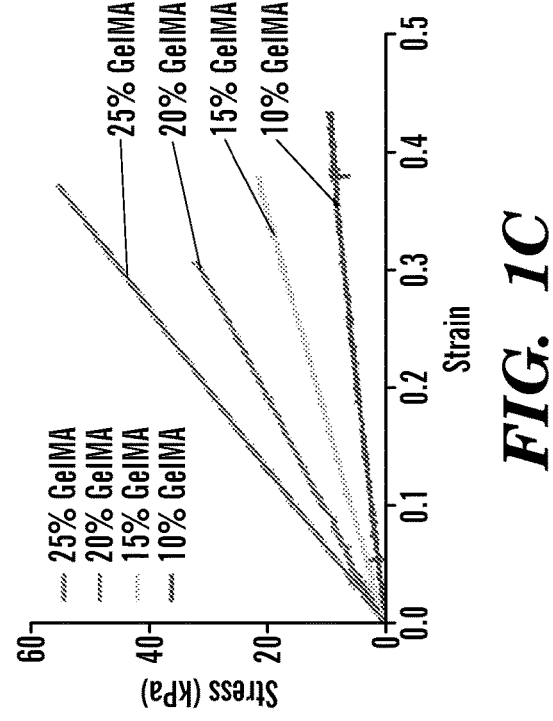

Prior to examination of the suitability of GelSEAL hydrogels to act as sealants, the material characteristics in dependency on different GelMA concentrations (10, 15, 20 and 25% (w/v), as produced in Example 1) were tested. Freshly photocrosslinked hydrogels and hydrogels soaked in phosphate buffered saline (PBS) for 24 hours underwent compressive mechanical testing. Under both conditions, higher GelMA concentrations resulted in steeper slopes of the stress-strain curves at lower strain (FIG. 1A) and increased compressive strength with the highest values for 25% (w/v) GelMA (FIG. 1B). Tensile testing also revealed steeper slopes of the stress-strain curves for higher GelMA concentrations (FIG. 1C) and increased ultimate tensile strength for 20 and 25% (w/v) GelMA (FIG. 1D). The swelling ratios of the hydrogels after 1, 2 and 3 days were significantly elevated for 10% GelMA as compared to higher concentrations (FIG. 1E). Scanning electron microscopy showed high porosity of the hydrogels (FIG. 1F).

Example 3: ASTM Standard In Vitro Testing of the Sealant Properties of GelSEAL

Properties that are important for effective sealants, i.e., wound closure strength, shear and burst resistance, were examined in vitro according to ASTM standard tests. In these tests, the performance of GelSEAL with different concentrations of GelMA and different photocrosslinking times (as produced in Examples 1 and 2) was compared to the clinically established sealants Evicel® (fibrin-based) and Coseal™ (poly(ethylene glycol)-based).

Wound Closure Strength Testing In Vitro

The wound closure strength of GelSEAL and the clinically established surgical sealants Evicel® (Ethicon, Somerville, N.J., USA) and Coseal™ (Baxter, Deerfield, Ill., USA) was examined referring to the ASTM standard test F2458-05 (standard test method for wound closure strength of tissue adhesives and sealants), whereas the standard method was slightly modified to fit a smaller sample size. In brief, fresh porcine skin from a local slaughterhouse was prepared by removing the adipose tissue layer and cutting the sample into rectangular sections measuring 5 mm*15 mm. While unused, porcine skin was kept moist in gauze soaked in PBS. Before use, porcine skin was blotted dry to remove excess liquid, and each end of the skin strip was fixed onto two poly(methyl methacrylate) slides (30 mm*60 mm) with Krazy glue (Westerville, Ohio, USA), leaving a 6 mm section of skin between the slides. The porcine skin strip was then cut apart using a razor blade [FIG. 2a-i], and petroleum jelly was applied with a syringe to the ends of the desired adhesive application area. Afterwards, 40 μl of the desired adhesive to be tested was applied across the 6 mm*5 mm skin section and, in case of GelSEAL, irradiated with UV light [FIG. 2a-ii]. After 1 hour of incubation in PBS, the two plastic slides were placed into the Instron system grips for tensile testing [FIG. 2a-iii]. The adhesive strength of a sealant sample was determined at the point of tearing. Each tested adhesive group contained four to seven samples.

Figure 2B:
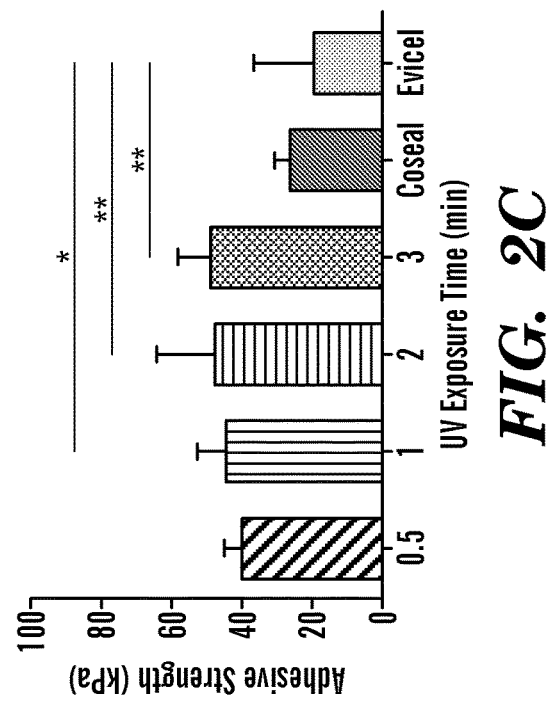
FIG. 2 depicts ASTM standard wound closure tests of GelSEAL hydrogels produced according to Examples 1-3. Schematic displaying porcine skin samples attached to poly (methyl methacrylate) slides (a.i), application and UV crosslinking of the GelSEAL tissue adhesive (a.ii) and subsequent tensile testing (a.iii). Representative stress-strain curves show higher tensile stiffness for GelSEAL when compared to the clinical standard adhesives Coseal™ and Evicel® (b,d), and for all tested crosslinking times, the adhesive strength of GelSEAL was significantly increased in comparison to the clinical standards (c). The best adhesive strength was achieved when using a GelSEAL concentration of 25% (e). *p<0.05; p<0.01; *p<0.001; ****p<0.0001.
Figure 2C:
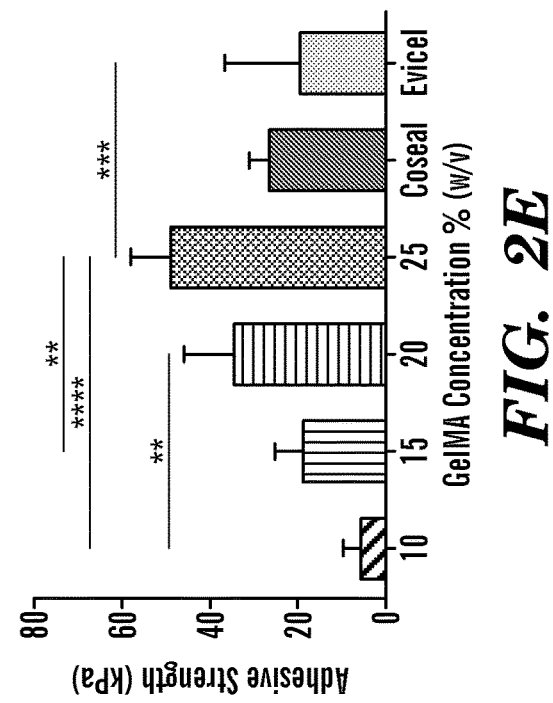
Figure 2D:
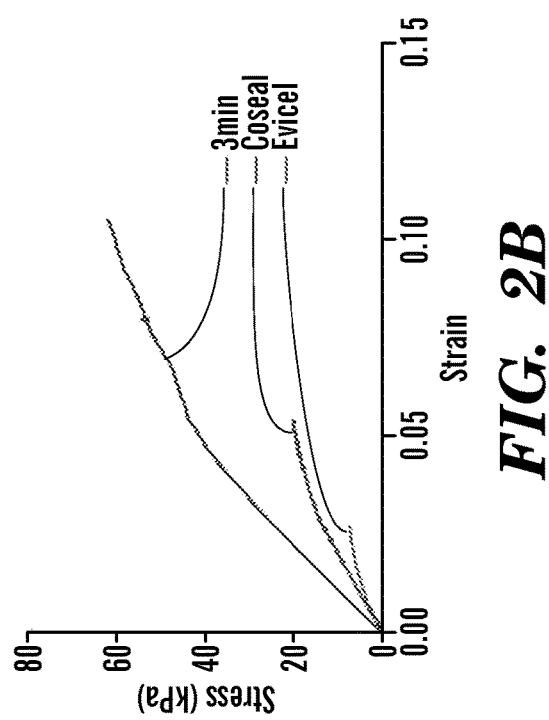
Figure 2E:
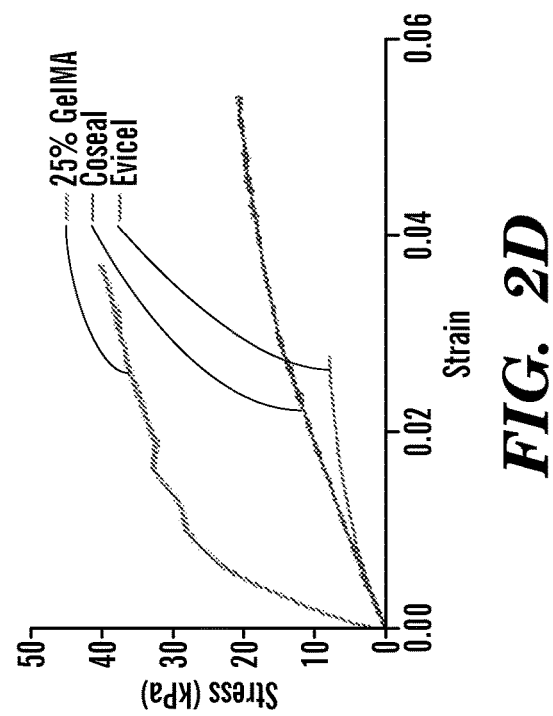

The wound closure strength was measured by tensile loading of adhesives sealing a standardized skin wound (FIG. 2A). GelSEAL allowed for higher strain before detaching and resisted more stress than both Evicel® and Coseal™ (FIG. 2B, 2D). The adhesive strength of GelSEAL photocrosslinked for 180 seconds and with 25% (w/v) GelMA concentration was increased as compared to clinical standard sealants as well as lower GelMA concentrations (FIGS. 2C, 2E).

Shear Resistance Testing In Vitro

The shear resistance of GelSEAL, Evicel® and Coseal™ was examined according to the ASTM standard test F2255-05 (standard test method for strength properties of tissue adhesives in lap-shear by tension loading). Gelatin coating was prepared by dissolving porcine gelatin in PBS at 80° C. The top region (10 mm*15 mm) of two glass slides (10 mm*50 mm in total) was coated with gelatin, which was allowed to dry at room temperature. Afterwards, 20 μl of the desired adhesive to be tested was applied on a 10 mm*10 mm area on top of the gelatin coating of one glass slide [FIG. 3a-i], after which another gelatin-coated glass slide was placed over the adhesive, in case of GelSEAL followed by irradiation with UV light [FIG. 3a-ii]. The two glass slides were placed into the Instron system grips for shear testing by tensile loading [FIG. 3a-iii]. The adhesive strength of a sealant sample was determined at the point of detaching. Each tested adhesive group contained five samples.

The shear resistance of the adhesives was analyzed by applying lap-shear by tensile loading (FIG. 3A). Longer photocrosslinking times and higher GelMA concentrations exhibited increased adhesive strength under lap-shear as compared to Coseal™ (FIGS. 3B, 3C). A UV light exposure time of 180 seconds and a GelMA concentration of 25% (w/v) revealed enhanced adhesive strength over Evicel®, whereas the difference was not statistically significant.

Burst Pressure Testing In Vitro

The burst pressure testing of GelSEAL, Evicel® and Coseal™ was adapted from the ASTM standard F2392-04 (standard test method for burst strength of surgical sealants). Collagen sheets (40 mm*40 mm) were soaked in PBS prior to sample preparation. A circular defect (3 mm in diameter) was created in the center of a collagen sheet that was placed between two Teflon sheets (35 mm*35 mm) [FIG. 4a-i]. The top Teflon sheet contained a hole (10 mm in diameter) to allow for application of the desired adhesive over the circular defect in the collagen sheet. In case of GelSEAL, the prepolymer was irradiated with UV light [FIG. 4a-ii]. Afterwards, the collagen sheet was removed and placed into the burst pressure testing system [FIG. 4a-iii], consisting of a pressure detection and recording unit and a syringe pump, which applied air with continuously increasing pressure towards the samples. Each tested adhesive group contained five samples.

Figure 4A:
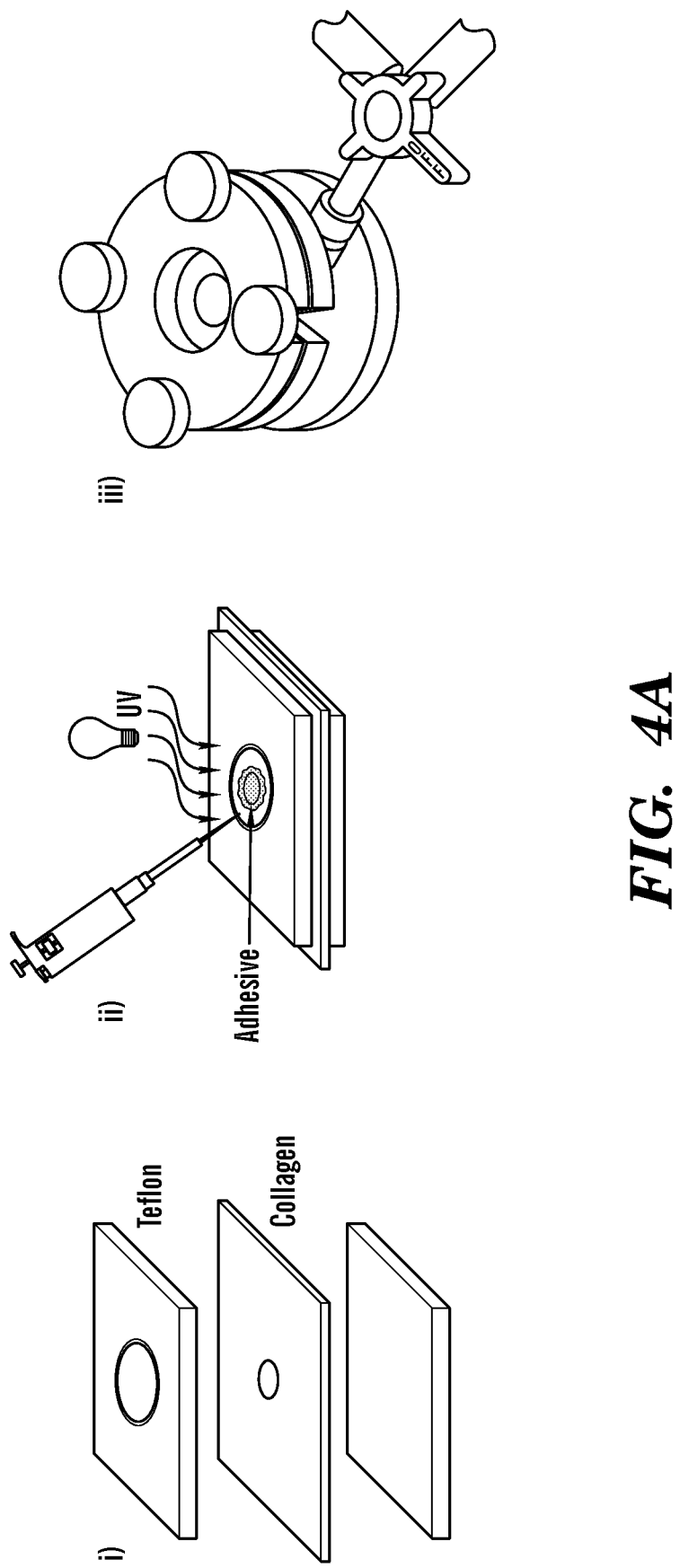
FIG. 4 depicts ASTM standard burst pressure tests of GelSEAL hydrogels produced according to Examples 1-3. Schematic displaying the arrangement of a defective collagen sheet between two poly(tetrafluoroethylene) sheets (a.i), application and UV crosslinking of the GelSEAL tissue adhesive (a.ii) and subsequent burst pressure measurement (a.iii). Representative burst pressure curves show higher burst levels for all tested crosslinking times (b) as well as for all tested GelSEAL concentrations (d) as compared to the clinical standards Coseal™ and Evicel®. A crosslinking time of 3 min (c) and a GelSEAL concentration of 25% (e) resulted in highly significantly improved burst pressure values. *p<0.05; p<0.01; *p<0.001; ****p<0.0001.
Figure 4C:
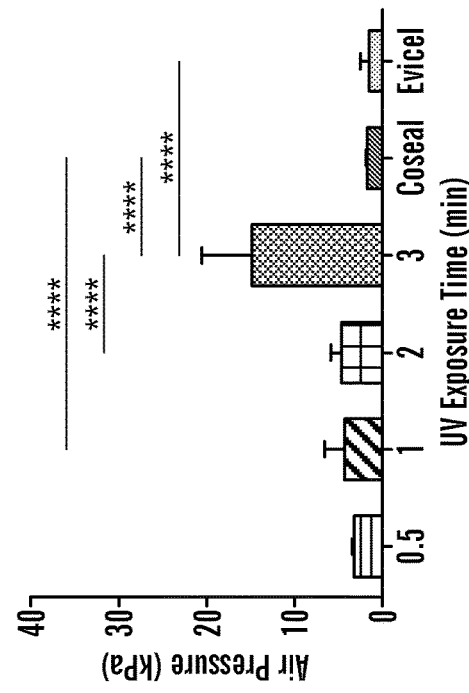
Figure 4E:
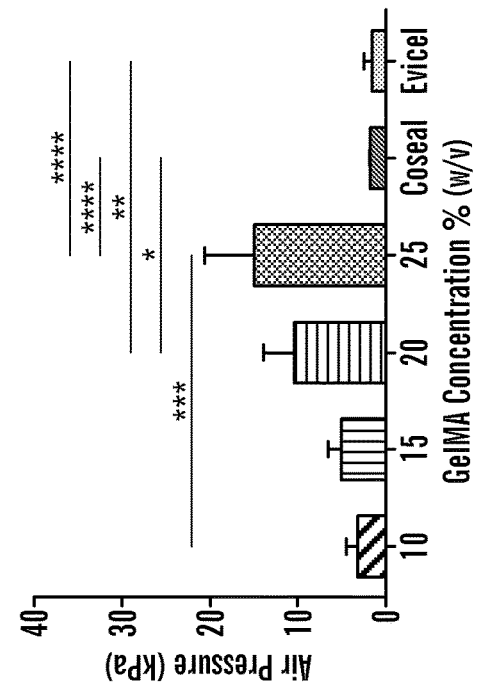
Figure 4B:
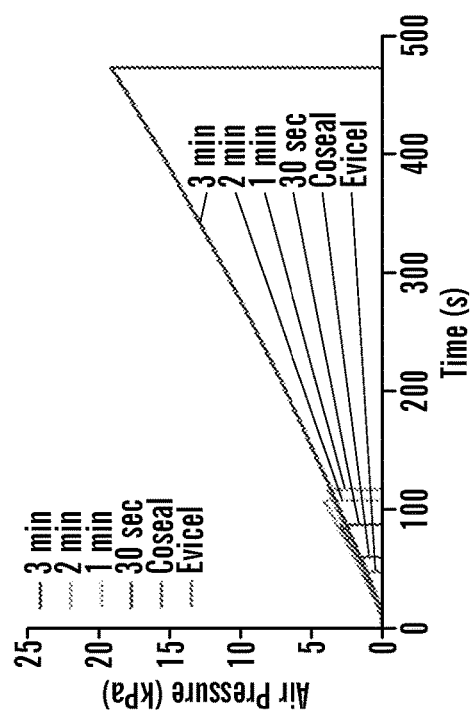
Figure 4D:
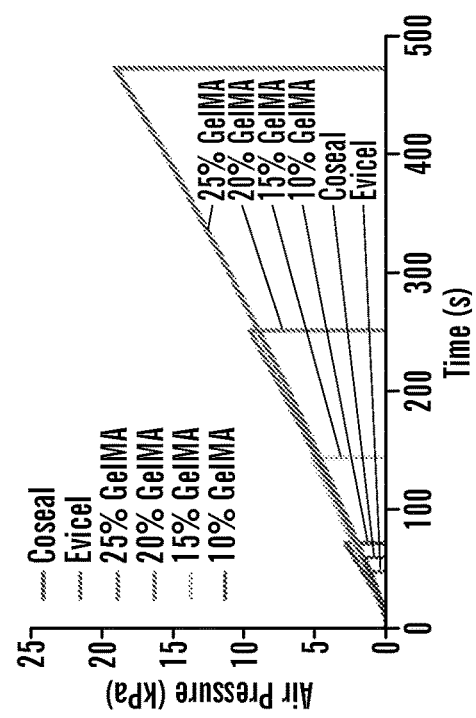

In order to test the burst resistance of the adhesives, continuously increasing air pressure was exerted on sealants covering a standardized defect in a collagen sheet (FIG. 4A). Each photocrosslinking time and each GelMA concentration resulted in higher burst pressure values for GelSEAL than Evicel® or Coseal™, whereas longer times and higher concentrations showed highly significantly increased pressure resistance (FIGS. 4B-4E).

Example 4: Biocompatibility of GelSEAL in Rats

Animal Experiments

All animal experiments were conducted in male Wistar rats weighing 200-250 g, obtained from Charles River (Wilmington, Mass., USA), housed in the local animal care facility (PRB, Cambridge, Mass., USA) and fed ad libitum. Anesthesia and analgesia were initiated and supported by isoflurane inhalation (2.0-2.5% (v/v)) and subcutaneous carprofen administration (5 mg/kg/d). All experiments strictly followed the NIH "Guide for the Care and Use of Laboratory Animals" and were approved by the local animal care committee (HMA Standing Committee on Animals; protocol number 05055).

Subcutaneous Implantation of GelSEAL in Rats

Subcutaneous implantation of GelSEAL in rats was conducted as recently published [GAHARWAR]. After induction of general anesthesia, small subcutaneous pockets were bluntly prepared through short dorsal skin incisions (10 mm in length), and 25% (w/v) (n=18) GelSEAL samples (as produced in Examples 1 and 2) were implanted. After anatomical wound closure, the animals were allowed to recover from anesthesia. After 3, 7 or 28 days, the animals were euthanized by $CO_2$ inhalation, and the implants including adjacent tissue were explanted and further processed for histology.

Figure 5A:
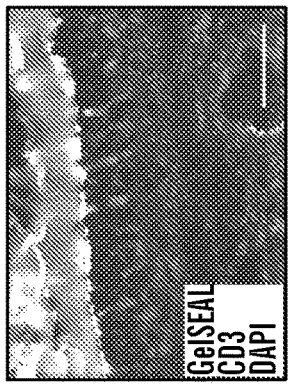
FIG. 5 depicts in vivo biocompatibility of GelSEAL hydrogels produced according to Examples 1 and 2. (Immuno)histology 3 (a-c), 7 (d-f) and 28 days (g-i) after subcutaneous implantation in rats showed initial implant-surrounding macrophage invasion (arrows in b,e) which was not present any more at day 28 (h). At no point, there were signs of lymphocyte infiltration (c,f,i). (a,d,g) hematoxylin-leosin staining; asterisks, GelSEAL; scale bars, 200 µm.
Figure 5B:
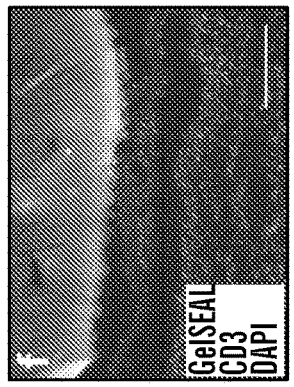
Figure 5C:
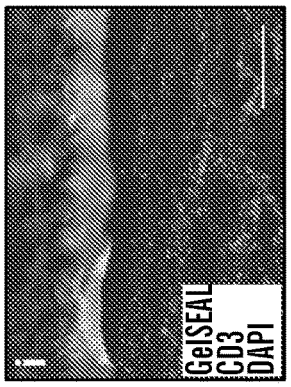
Figure 5D:
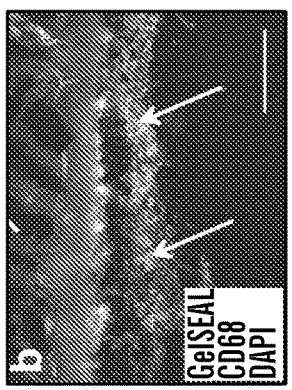
Figure 5E:
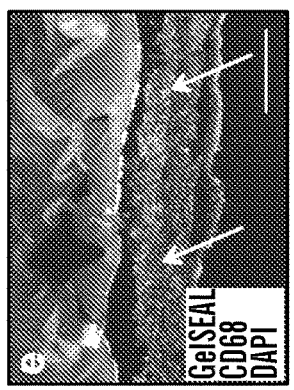
Figure 5F:
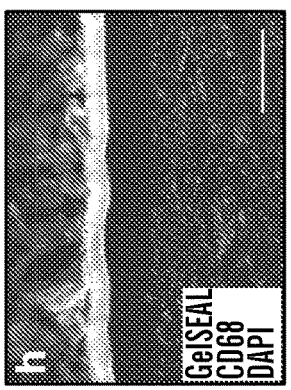
Figure 5G:
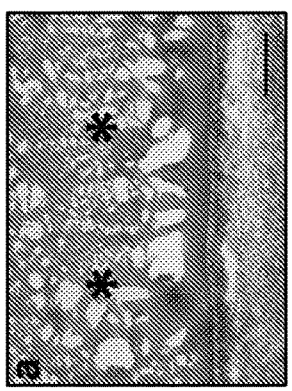
Figure 5H:
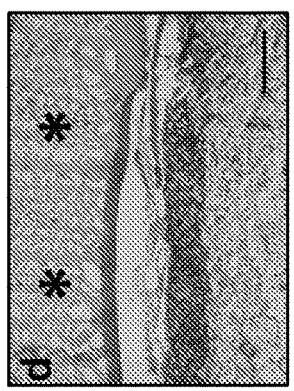
Figure 5I:
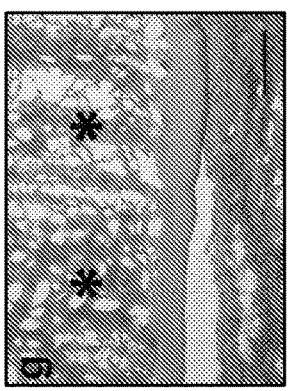

The general biocompatibility of GelSEAL was examined 3, 7 and 28 days after subcutaneous implantation of the hydrogels in rats. At days 3 and 7, macrophages were observed around the implants (FIGS. 5B, 5E) however, at day 28, they were not present any more (FIG. 5H). No lymphocyte infiltration was detected at any time point (FIGS. 5C, 5F, 5I). Thus, the beneficial biocompatibility of gelatin is not impaired by methacrylation and UV light-mediated crosslinking To the best of the inventors' knowledge, this is the first report on the inflammatory host response against GelMA/GelSEAL implants.

Example 5: GelSEAL as Sealant for Lung Leakages In Vivo

In order to examine the suitability and effectiveness of GelSEAL as sealant for lung leakages in vivo, a rat model was developed based on previous literature [KOBAYASHI]. After induction of inhalative anesthesia, rats were orally intubated and subsequently ventilated (frequency 80 per minute; tidal volume 3 ml) maintaining isoflurane anesthesia. Through a right lateral thoracotomy in the sixth intercostal space, a standardized lung lobe incision (3 mm in length; 5 mm in depth towards the hilum) was generated with a no. 11 surgical blade. All animals showed outbreak of air bubbles and small amounts of blood through the incisions. Immediately, under ventilation arrest, 50 μl GelSEAL (as produced in Examples 1 and 2) (n=7) or Evicel (n=3) was administered [FIG. 6a] and cured for 30 seconds, in case of GelSEAL under UV light [FIG. 6b]. After having re-established ventilation, leakage from the sealed injury was tested by application of warm saline solution, whereas no leakage was detected after single use of the sealants in any of the animals. The thorax was anatomically closed, followed by de-airing of the pleural space by means of a custom-made thorax drainage system [FIG. 6c]. In case of chronic experiments, animals were allowed to recover from anesthesia under sustained ventilation.

Directly after defect sealing (n=6) or at days 7 (n=3) or 28 (n=1), the animals were humanely euthanized, and burst pressure measurements were conducted immediately. Here, the trachea was occlusively intubated and connected to a split tubing system linking a pressure detection and recording unit and a syringe pump with the lungs of the rat [FIG. 6d]. Under continuous air injection, the lungs were inflated, and the increasing pressure was recorded up to the point of material burst or detachment or tissue burst. The time point and type of sealant failure was additionally visualized by conducting the experiment in a water bath, resulting in air bubbles rising from the leakage site. Burst pressure measurements in non-injured lungs (n=3) served as additional controls.

Figure 6A:
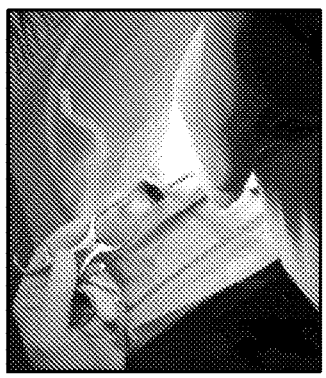
FIG. 6 depicts in vivo lung leakage sealing capacity of GelSEAL hydrogels produced according to Examples 1 and 2. Rat lung leakage model (a-c): GelSEAL is applied on a lung leakage via a small lateral thoracotomy (a). After UV crosslinking of the tissue adhesive (b), the chest is closed and a chest tube for de-airing is inserted into the pleura (c). Schematic of the burst pressure setting for measurements after lung leakage sealing (d): A syringe pump and a pressure sensor are connected to the trachea allowing for pressure monitoring during lung inflation in a closed system. Representative picture showing GelSEAL on the lung leakage after pressure drop induced by partial detachment of GelSEAL from the lung surface (e). Representative picture displaying Evicel® on the lung leakage after pressure drop induced by central bursting of Evicel® (f). Immediately after material application, the burst pressure of GelSEAL was significantly higher than the one of Evicel® (g). In the follow-up, the initially high burst pressure of GelSEAL was even enhanced and reached the level of healthy lung tissue at day 7 (h). (b,c) air bubbles emerging from the submersed lung indicate the site and type of material failure. *p<0.05.
Figure 6B:
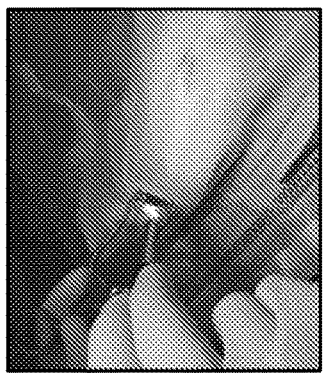
Figure 6C:
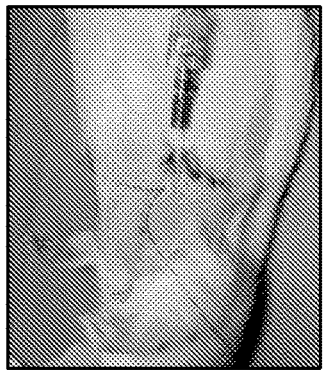
Figure 6D:
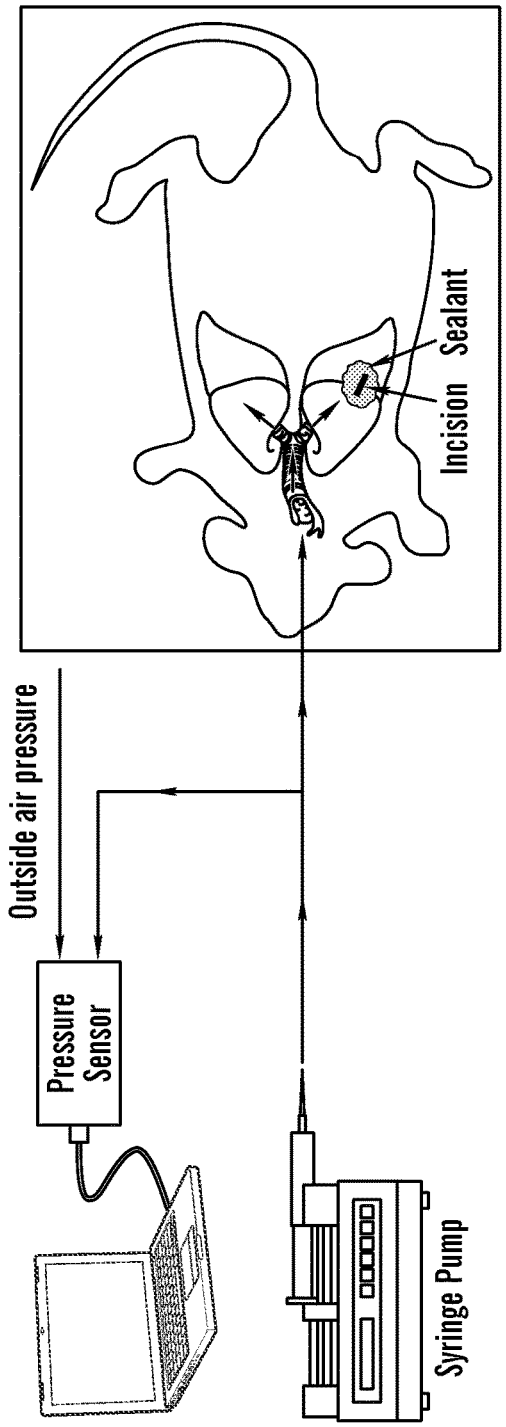
Figure 6E:
Figure 6F:
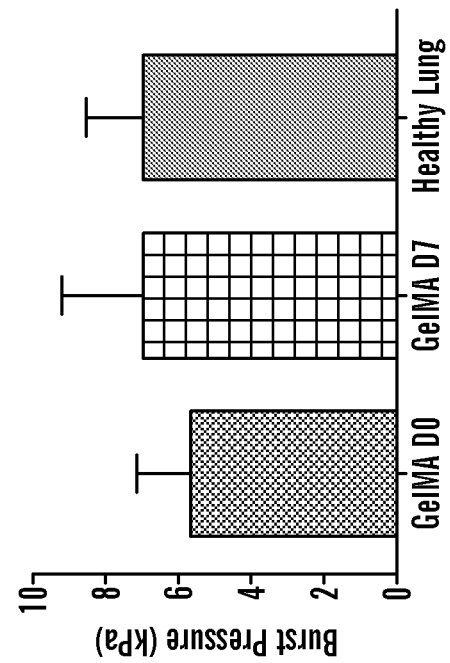
Figure 6G:
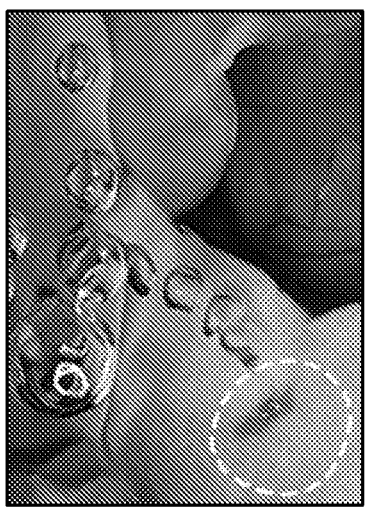
Figure 6H:
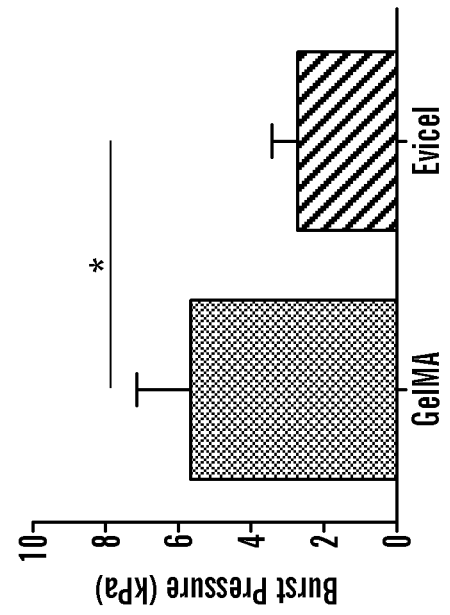

A rat model of standardized lung leakage was established to test the suitability and effectiveness of GelSEAL as in vivo sealant for pulmonary lesions in the absence of any additional conventional surgical methods, as e.g., suturing or stapling (FIGS. 6A-6C). The initial sealing strength as well as the postoperative performance of GelSEAL during autologous defect repair until postoperative day 28 was examined. All rats survived the surgery and the desired follow-up period. No clinical signs of postoperative pneumothorax were observed, and at the end of the follow-up period, no lung leakage was found. In order to quantify the sealing strength, burst pressure measurements were conducted (FIG. 6D). In case of GelSEAL, the typical mode of failure was not bursting of the material, but detachment from the lung surface (FIG. 6E). On the contrary, Evicel® failed by material burst (FIG. 6F). The burst pressure of GelSEAL directly after curing was significantly increased as compared to Evicel® (FIG. 6G). After 7 days, the burst pressure was even further elevated and reached values that were equal to the burst pressure of native rat lung tissue (FIG. 6H). In fact, in two of three GelSEAL-treated lungs at day 7, not the sealant failed, but the native lung tissue burst in another area. At day 28, no GelSEAL remnants and no defect site could be macroscopically found on the lung. Besides adequate wound healing, biodegradation of the sealant is implied, which might be achieved by host collagenases, i.e., primarily the matrix metalloproteinases 1, 8 and 13.

Example 6: Synthesis of Dopamine-Conjugated GelMA

Gelatin was added at a final concentration of 2 mg/ml to water. 1 mM of BOP ((benzotriazol-1-yloxy)tris(dimethylamino)phosphonium hexafluorophosphate), 1 mM of HOBt (1-hydroxybenzotriazole), 10 mM of dopamine hydrochloride, and 12 mM of triethylamine were then added. The reaction mixture was mixed with stir bar for 2 hr under $N_2$. The dopylated gelatin was precipitated with cold acetone. The obtained dopylated gelatin was then acrylated by using metacrylic anhydride as previously described [Nichol J W, Koshy S T, Bae H, Hwang C M, Yamanlar S, Khademhosseini A. Cell-laden microengineered gelatin methacrylate hydrogels. Biomaterials. 2010; 31(21):5536-44. doi: S0142-9612(10)00448-5 [pii]10.1016/j.biomaterials.2010.03.064. PubMed PMID: 20417964; PubMed Central PMCID: PMC2878615]. Briefly, dopylated gelatin was dissolved in PBS at concentration of 10% (w/v) and heated at 60° C. for 20 minutes. Drop wise addition of 8% (v/v) methacrylic anhydride (Sigma-Aldrich, St. Louis, Mo., USA) under continuous stirring at 50° C. for 3 hours was followed by dilution with PBS and dialysis against deionized water at 40-50° C. for 7 days. After sterile filtration and lyophilization for 4 days, GelMA-Dopamine was stored at −80° C. until experimental use.

Example 7: Preparation and Material Characterization of Visible Light Crosslinkable Dopamine-Conjugated GelMA Sealant Different concentrations of GelMA (10, 15, 20% (w/v)) and GelMA-Dopamine (15% w/v) were tested for material characterization. Freeze-dried GelMA (as produced in Example 1) and GelMA-Dopamine (as produced in Example 6) were dissolved in PBS containing 1.875% (w/v) triethanolamine (TEA) and 1.25% (w/v) N-vinylcaprolactam (VC) at concentrations of 10, 15, 20 (w/v). Eosin Y was separately dissolved in fresh DPBS at a concentration of 0.5 mM. To prepare the hydrogel, 8 μL of GelMA or GelMA-Dopamine solution was mixed with 2 μL of Eosin Y solution, and then the mixture was placed between two glass coverslips separated by 150 μm spacers, followed by exposed to blue-green light (100 mW/cm$^2$, Xenon source from Genzyme Biosurgery) in the range of 450 to 550 nm for 20 sec.

Mechanical Characterization

Figure 7B:
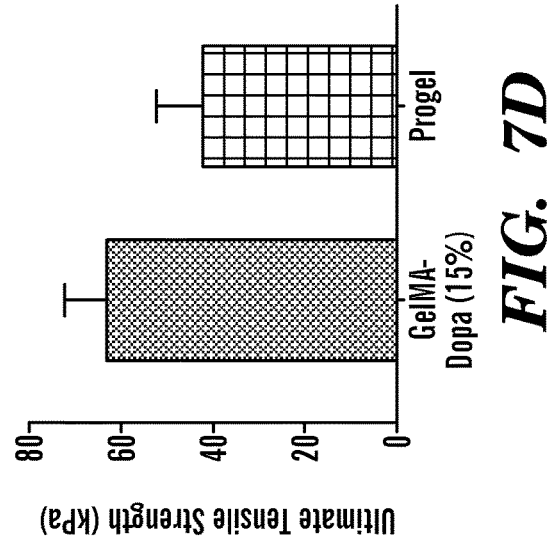
FIG. 7 depicts a) a representative curve for GelMA-Dopamine's compressive strength; b) polymer compressive strength at different concentrations of GelMA as produced in Example 7; c) representative tensile strength curves for Progel and GelMA-Dopamine; and d) ultimate tensile strength of GelMA-Dopamine and Progel.
Figure 7D:
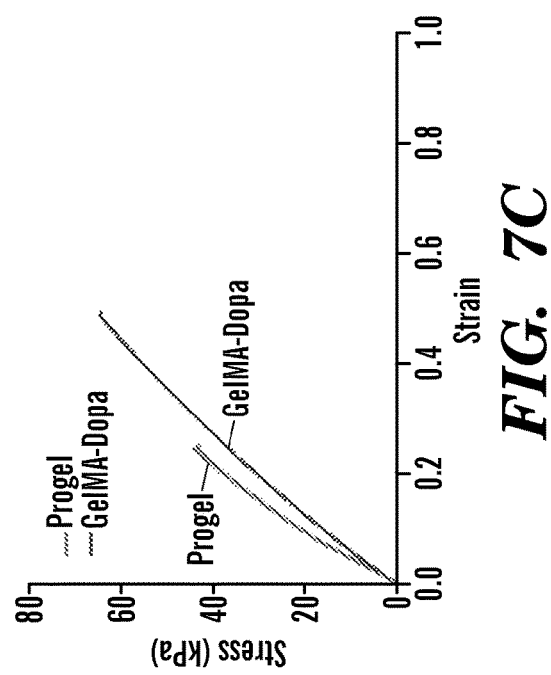
Figure 7A:
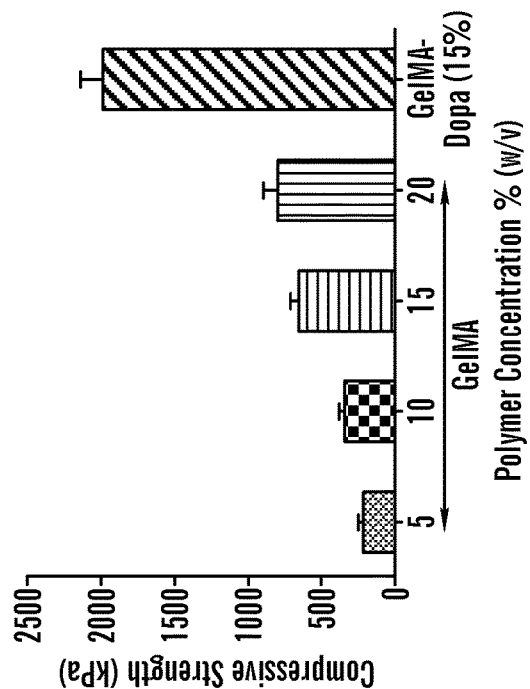
Figure 7C:
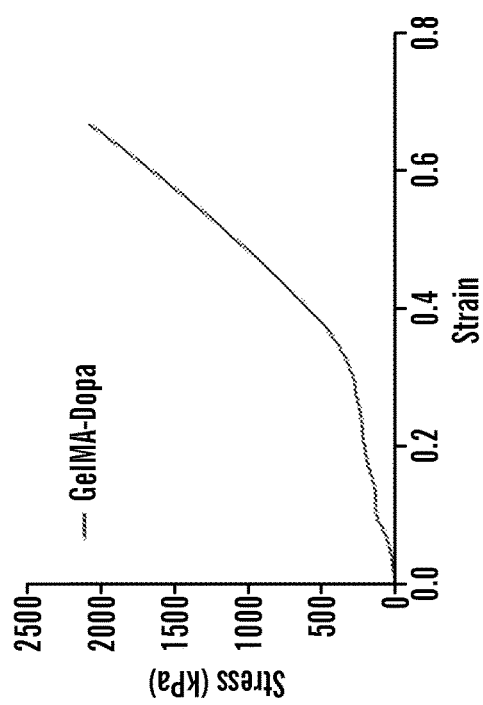

Freshly photocrosslinked hydrogels underwent compressive mechanical testing. Steeper slopes of the stress-strain at lower strain [FIG. 7a] were resulted at higher concentrations of GelMA and GelMA-Dopamine. Highest compressive value was obtained at 15% (w/v) GelMA-Dopamirne hydrogel [FIG. 7b]. Steeper slopes of the stress-strain tensile curves were revealed for GelMA. Dopamine (15% (w/v)) compared to Progel™ as commercially available surgical glues [FIG. 7c] Moreover, higher tensile strength was obtained for GelMA-Dopamine in contrast to Progel™ [FIG. 7d].

Burst Pressure

Figure 8D:
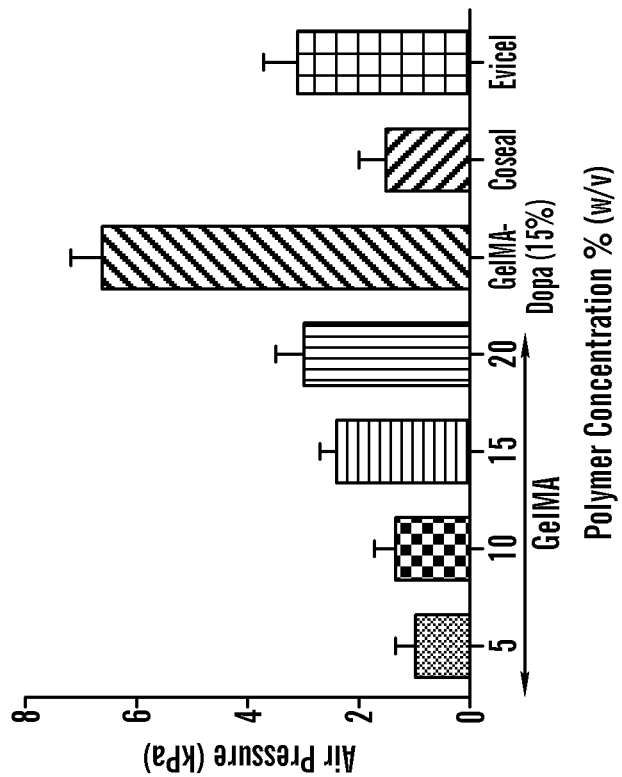
FIG. 8 depicts a) a schematic of the sample preparation for burst pressure testing; b) top view of the burst pressure test setup (prepared collagen sheet is placed between the metal plates); c) representative burst pressure curves for GelMA-Dopamine and GelMA compared to CoSeal and Evicel; and d) said sealants' burst pressures. GelMA-Dopamine and GelMA were produced according to Examples 6 and 7.

The burst pressure testing of sealants was adapted from the ASTM standard F2392-04 (standard test method for burst strength of surgical sealants). Porcine skin sheets (40 mm*40 mm) were soaked in PBS prior to sample preparation. A circular defect (3 mm in diameter) was created in the center of a pig skin sheet that was placed between two Teflon sheets (35 mm*35 mm). The top Teflon sheet contained a hole (10 mm in diameter) to allow for application of the desired adhesive over the circular defect in the porcine skin sheet [FIG. 8a]. In the case of GelMA and GelMA-Dopamine the prepolymer was irradiated with visible light. Afterwards, the collagen sheet was removed and placed into the burst pressure testing system, consisting of pressure detection and recording unit and a syringe pump, which applied air with continuously increasing pressure towards the samples [FIG. 8b] Each tested adhesive group contained five samples.

Figure 8C:
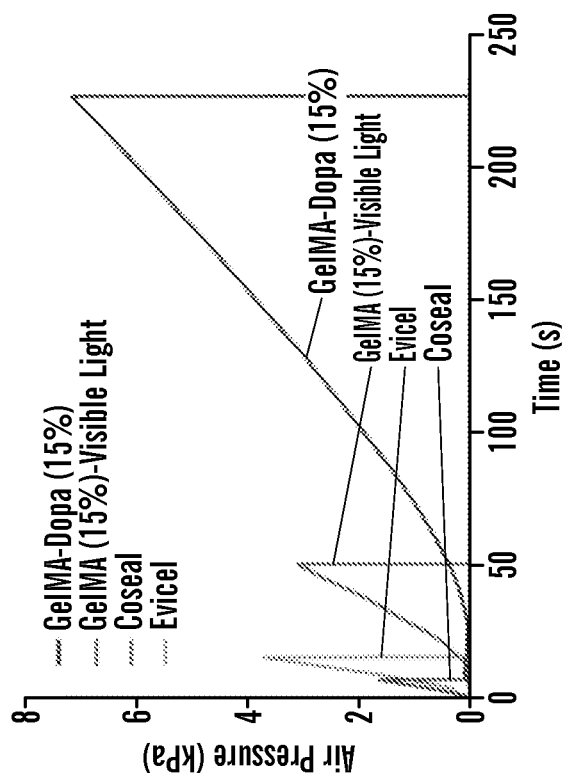

Increasing air pressure was applied on sealant covering a standardized defect in porcine skin to test the burst pressure resistance [FIG. 8c]. Each GelMA concentration resulted in higher burst pressure values than Coseal™. GelMA-Dopamine hydrogel (15% (w/v)) showed highest burst pressure compare to GelMA, Evicel® and Coseal™ [FIG. 8d].

Wound Closure

The wound closure strengths of GelMA and GelMA-Dopamine and the clinically established surgical sealants Evicel® (Ethicon, Somerville, N.J., USA), Coseal™ (Baxter, Deerfield, Ill. USA) and Progel™ were examined referring to the ASTM standard test F2458-05 (standard test method for wound closure strength of tissue adhesives and sealants), whereas the standard method was slightly modified to fit a smaller sample size. In brief, fresh porcine skin from a local slaughterhouse was prepared by removing the adipose tissue layer and cutting the sample into rectangular sections measuring 5 mm*15 mm. While unused, porcine skin was kept moist in gauze soaked in PBS. Before use, porcine skin was blotted dry to remove excess liquid, and each end of the skin strip was fixed onto two poly (methyl methacrylate) slides (30 mm*60 mm) with Krazy glue (Westerville, Ohio, USA) leaving a 6 mm section of skin between the slides. The porcine skin strip was then cut apart using a razor blade [FIG. 9a], and petroleum jelly was applied with a syringe to the ends of the desired adhesive application area. Afterwards, 40 μl of the adhesive was applied across the 6 mm*5 mm skin section and, in case of GelMA and GelMA-Dopamine, irradiated with visible light [FIG. 9a]. After 1 hour of incubation in PBS, the two plastic slides were placed into the Instron system grips for tensile testing [FIG. 9a]. The adhesive strength of a sealant sample was determined at the point of tearing Each tested adhesive group contained four to seven samples.

Figure 9A:
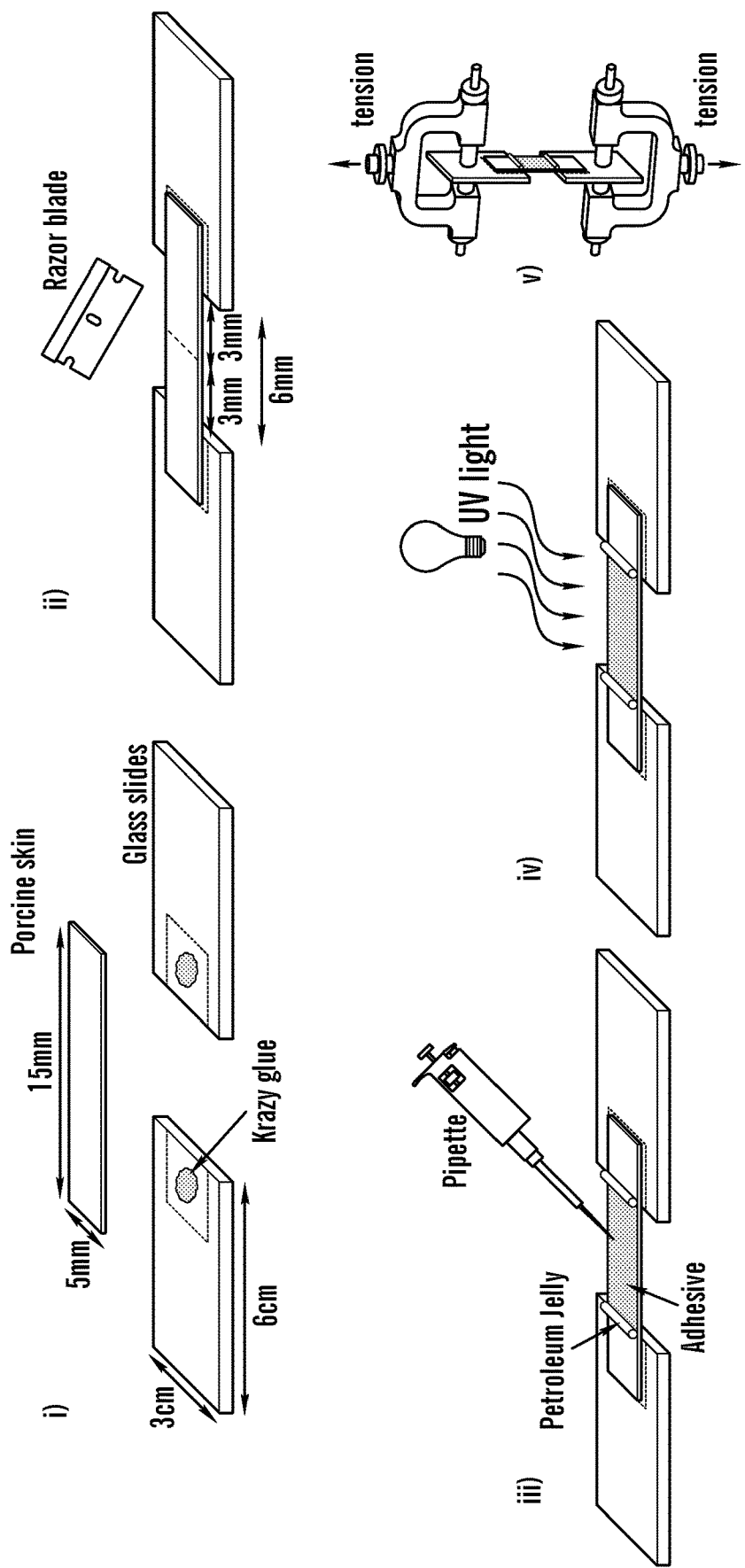
FIG. 9 depicts a) a schematic of the modified standard test method for wound closure strength (ASTM F2458-05); b) representative adhesive curves for GelMA-Dopamine and GelMA compared to Progel, CoSeal, and Evicel; and c) Adhesive strength of said sealants using the wound closure test. GelMA-Dopamine and GelMA were produced according to Examples 6 and 7.
Figure 9C:
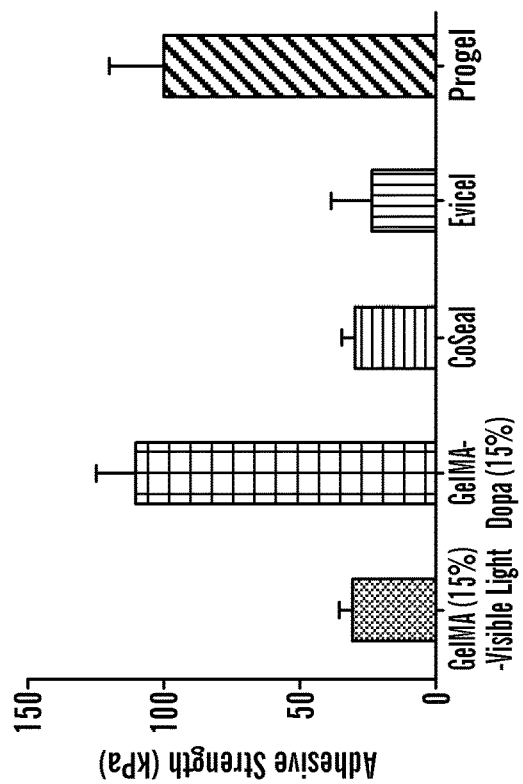
Figure 9B:
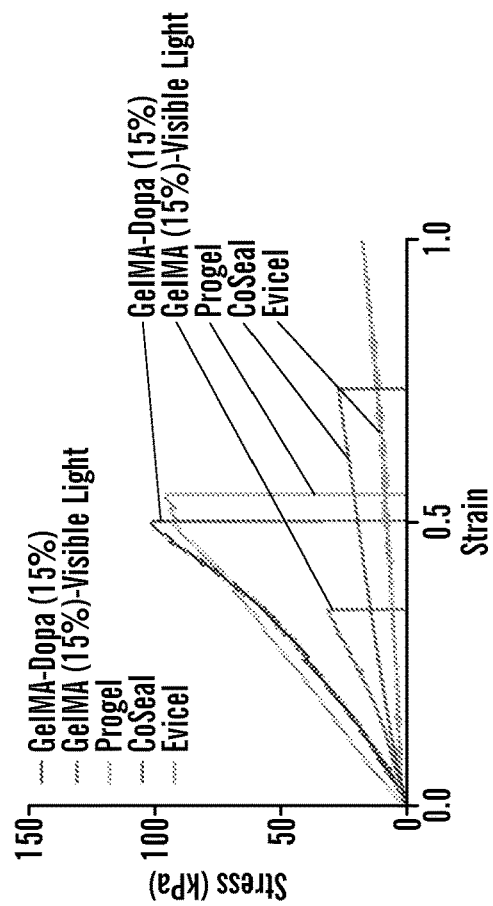

The wound closure strength was measured by tensile loading of adhesives sealing a standardized skin wound [FIG. 9a]. Higher strain obtained by GelMA-Dopamine before detaching and resisted more stress than Progel™, Evicel® and Coseal™ [FIGS. 9b and 9c], The adhesive strength or GelMA-Dopamine with 15% (w/v) concentration was higher as compared to clinical standard sealants as well as GelMA sealant [FIGS. 9b and 9c].

Lap Shear Test

The shear resistance of sealants was examined according to the ASTM standard test F2255. 05 (standard test method for strength properties of tissue adhesives in lap-shear by tension loading) Gelatin coating was prepared by dissolving porcine gelatin in PBS at 80° C. The top region (10 mm*15 mm) of two glass slides (10 mm*50 mm in total) was coated with gelatin, which was allowed to dry at room temperature. Afterwards, 20 μl of the desired adhesive to be tested was applied on a 10 mm*10 mm area on top of the gelatin coating of one glass slide [FIG. 10a], after which another gelatin. coated glass slide was placed over the adhesive, in case of GelMA and GelMA-Dopamine followed by irradiation with visible light. The two glass slides were placed into the Instron system grips for shear testing by tensile loading. The adhesive strength of a sealant sample was determined at the point of detaching. Each tested adhesive group contained five samples.

The ASTM standard lap-shear test was used to analyze the shear resistance of the adhesive [FIG. 10a]. Higher GelMA concentrations exhibited increased adhesive strength under lap-shear as compared to Coseal™ [FIG. 10b]. GelMA-Dopamine (15% (w/v)) showed an extraordinary adhesive strength under lap shear test compare to Progel™, Evicel® and Coseal™ [FIG. 10b]. The lap shear strength for GelMA-Dopamine reached 800 kpa while the maximum strength for Progel™ sealant was less than 300 kpa [FIG. 10b].

Example 8: Ex Vivo Model for Minimally Invasive Sealing of Lung

Figure 11A:
FIG. 11 depicts an ex vivo pig model of standardized trachea leakage: a) trachea before making a hole; b) trachea after making a hole; c) camera view of trachea before applying glue; d) camera view of trachea after applying GelMA-visible light (15%); e) camera view of trachea after applying GelMA-Dopamine (15%); and f) burst pressure of GelMA-visible light (15%) and GelMA-Dopamine visible light (15%). GelMA-Dopamine and GelMA were produced according to Examples 6 and 7.
Figure 11B:
Figure 11C:
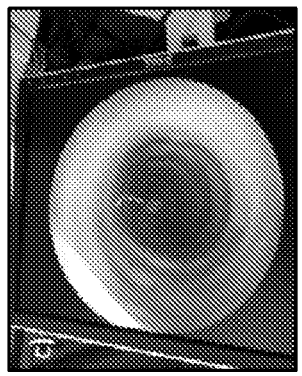
Figure 11D:
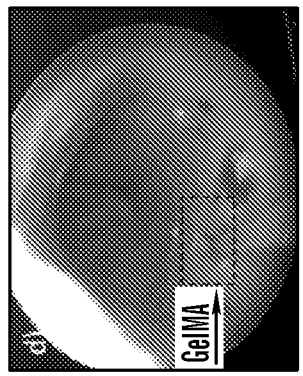
Figure 11E:
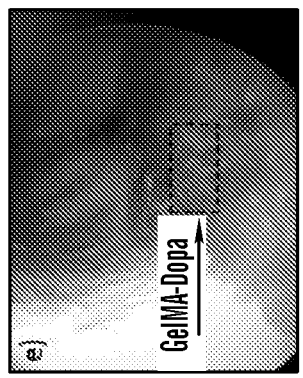
Figure 11F:
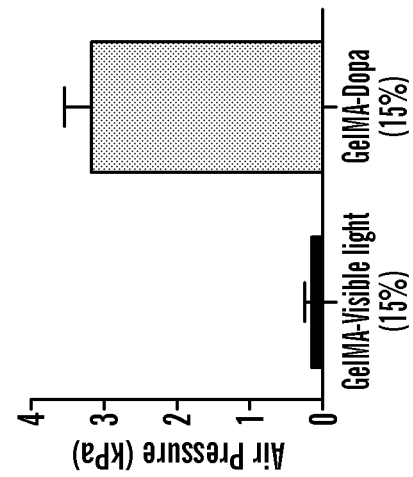

A pig model of standardized Trachea leakage was established to test the suitability and effectiveness of GelMA and GelMA-Dopamine (as produced in Examples 6 and 7) as minimally invasive sealant for pulmonary lesions in the absence of any additional conventional surgical methods as e.g. suturing or stapling [FIGS. 11a-11e]. In order to quantify the sealing strength, burst pressure measurements were conducted [FIG. 11f]. In case of GelMA, the typical mode of failure was bursting of the material at the air pressure resistance of 0.3 kpa. However, For GelMA-Dopamine the air pressure resistance of 3.5 kpa was obtained which shows better performance of GelMA-Dopamine compare to GelMA [FIG. 11f].

REFERENCES

Itano H. The optimal technique for combined application of fibrin sealant and bioabsorbable felt against alveolar air leakage. Eur J Cardiothorac Surg. 2008 March; 33(3): 457-60. doi: 10.1016/j.ejcts.2007.12.036. Epub 2008 Feb. 1.

Glickman M, Gheissari A, Money S, Martin J, Ballard J L; CoSeal Multicenter Vascular Surgery Study Group. A polymeric sealant inhibits anastomotic suture hole bleeding more rapidly than gelfoam/thrombin: results of a randomized controlled trial. Arch Surg. 2002 March; 137(3):326-31; discussion 332.

Annabi N, Tamayol A, Shin S R, Ghaemmaghami A M, Peppas N A, Khademhosseini A. Surgical Materials: Current Challenges and Nano-enabled Solutions. Nano Today. 2014 Oct. 1; 9(5):574-589.

Wolbank S, Pichler V, Ferguson J C, Meinl A, van Griensven M, Goppelt A, Redl H. Non-invasive in vivo tracking of fibrin degradation by fluorescence imaging. J Tissue Eng Regen Med. 2014 Jul. 6. doi: 10.1002/term.1941. [Epub ahead of print]

Montanaro L, Arciola C R, Cenni E, Ciapetti G, Savioli F, Filippini F, Barsanti L A. Cytotoxicity, blood compatibility and antimicrobial activity of two cyanoacrylate glues for surgical use. Biomaterials. 2001 January; 22(1):59-66.

Spotnitz W D, Burks S. Hemostats, sealants, and adhesives III: a new update as well as cost and regulatory considerations for components of the surgical toolbox. Transfusion. 2012 October; 52(10):2243-55. doi: 10.1111/j.1537-2995.2012.03707.x. Epub 2012 May 21.

Bitton R, Josef E, Shimshelashvili I, Shapira K, Seliktar D, Bianco-Peled H. Phloroglucinol-based biomimetic adhesives for medical applications. Acta Biomater. 2009 June; 5(5):1582-7. doi: 10.1016/j.actbio.2008.10.004. Epub 2008 Oct. 22.

Mehdizadeh M, Weng H, Gyawali D, Tang L, Yang J. Injectable citrate-based mussel-inspired tissue bioadhesives with high wet strength for sutureless wound closure. Biomaterials. 2012 November; 33(32):7972-83. doi: 10.1016/j.biomaterials.2012.07.055. Epub 2012 Aug. 16.

Park E L, Ulreich J B, Scott K M, Ullrich N P, Linehan J A, French M H, Ho W Y, White M J, Talley J R, Fellah A M, Ramakumar S. Evaluation of polyethylene glycol based hydrogel for tissue sealing after laparoscopic partial nephrectomy in a porcine model. J Urol. 2004 December; 172(6 Pt 1):2446-550.

Than K D, Baird C J, Olivi A. Polyethylene glycol hydrogel dural sealant may reduce incisional cerebrospinal fluid leak after posterior fossa surgery. Neurosurgery. 2008 July; 63(1 Suppl 1):ONS182-6; discussion ONS186-7. doi: 10.1227/01.neu.0000335034.08274.d2.

Shazly T M, Artzi N, Boehning F, Edelman E R. Viscoelastic adhesive mechanics of aldehyde-mediated soft tissue sealants. Biomaterials. 2008 December; 29(35):4584-91. doi: 10.1016/j.biomaterials.2008.08.032. Epub 2008 Sep. 19.

Tessmar J K, Gopferich A M. Customized PEG-derived copolymers for tissue-engineering applications. Macromol Biosci. 2007 Jan. 5; 7(1):23-39.

Buskens E, Meijboom M J, Kooijman H, Van Hout B A. The use of a surgical sealant (CoSeal) in cardiac and vascular reconstructive surgery: an economic analysis. J Cardiovasc Surg (Torino). 2006 April; 47(2):161-70.

Cha C, Shin S R, Gao X, Annabi N, Dokmeci M R, Tang X S, Khademhosseini A. Controlling mechanical properties of cell-laden hydrogels by covalent incorporation of graphene oxide. Small. 2014 Feb. 12; 10(3):514-23. doi: 10.1002/smll.201302182. Epub 2013 Oct. 11.

Nichol J W, Koshy S T, Bae H, Hwang C M, Yamanlar S, Khademhosseini A. Cell-laden microengineered gelatin methacrylate hydrogels. Biomaterials. 2010 July; 31(21): 5536-44.

Shin S R, Bae H, Cha J M, Mun J Y, Chen Y C, Tekin H, Shin H, Farshchi S, Dokmeci M R, Tang S, Khademhosseini A. Carbon nanotube reinforced hybrid microgels as scaffold materials for cell encapsulation. ACS Nano. 2012 Jan. 24; 6(1):362-72. doi: 10.1021/nn203711s. Epub 2011 Dec. 20.

Visser J, Gawlitta D, Benders K E, Toma S M, Pouran B, van Weeren P R, Dhert W J, Malda J. Endochondral bone formation in gelatin methacrylamide hydrogel with embedded cartilage-derived matrix particles. Biomaterials. 2014 Oct. 23; 37C:174-182. doi: 10.1016/j.biomaterials.2014.10.020. [Epub ahead of print]

Hjortnaes J, Camci-Unal G, Hutcheson J D, Jung S M, Schoen F J, Kluin J, Aikawa E, Khademhosseini A. Directing Valvular Interstitial Cell Myofibroblast-Like Differentiation in a Hybrid Hydrogel Platform. Adv Healthc Mater. 2014 Jun. 24. doi: 10.1002/adhm.201400029. [Epub ahead of print]

Nikkhah M, Eshak N, Zorlutuna P, Annabi N, Castello M, Kim K, Dolatshahi-Pirouz A, Edalat F, Bae H, Yang Y, Khademhosseini A. Directed endothelial cell morphogenesis in micropatterned gelatin methacrylate hydrogels. Biomaterials. 2012 December; 33(35):9009-18. doi: 10.1016/j.biomaterials.2012.08.068. Epub 2012 Sep. 24.

Gaharwar A K, Avery R K, Assmann A, Paul A, McKinley G H, Khademhosseini A, Olsen B D. Shear-Thinning Nanocomposite Hydrogels for the Treatment of Hemorrhage. ACS Nano. 2014; 8(10):9833-9842.

Kobayashi H, Sekine T, Nakamura T, Shimizu Y. In vivo evaluation of a new sealant material on a rat lung air leak model. J Biomed Mater Res. 2001; 58(6):658-65.

Assmann, A., Zwirnmann K, Heidelberg F, Schiffer F, Horstkotter K, Munakata H, Gremse F, Barth M, Lichtenberg A, Akhyari P. The degeneration of biological cardiovascular prostheses under pro-calcific metabolic conditions in a small animal model. Biomaterials 35, 7416-7428 (2014).

Elvin C M, Vuocolo T, Brownlee A G, Sando L, Huson M G, Liyou N E, Stockwell P R, Lyons R E, Kim M, Edwards G A, Johnson G, McFarland G A, Ramshaw J A, Werkmeister J A. A highly elastic tissue sealant based on photopolymerised gelatin. Biomaterials. 2010 November; 31(32):8323-31. doi: 10.1016/j.biomaterials.2010.07.032. Epub 2010 Aug. 1.

Teng R, Johkura K, Ogiwara N, Zhao X, Cui L, Iida I, Okouchi Y, Asanuma K, Sasaki K. Morphological analysis of leucocyte transmigration in the pleural cavity. J Anat. 2003 October; 203(4):391-404.

Anegg U, Lindenmann J, Matzi V, Smolle J, Maier A, Smolle-Jiittner F. Efficiency of fleece-bound sealing (TachoSil) of air leaks in lung surgery: a prospective randomised trial. Eur J Cardiothorac Surg. 2007 Feburary; 31(2):198-202. Epub 2006 Dec. 21.

Qerimi B, Baumann P, Hiising J, Knaebel H P, Schumacher H. Collagen hemostat significantly reduces time to hemostasis compared with cellulose: COBBANA, a single-center, randomized trial. Am J Surg. 2013 June; 205(6): 636-41. doi: 10.1016/j.amjsurg.2012.05.033. Epub 2013 Jan. 17.

Katagiri Y, Brew S A, Ingham K C. All six modules of the gelatin-binding domain of fibronectin are required for full affinity. J Biol Chem. 2003 Apr. 4; 278(14):11897-902. Epub 2003 Jan. 21.

Gorgieva, S.; Kokol, V. Collagen- vs. Gelatine-Based Biomaterials and Their Biocompatibility: Review and Perspectives. In Biomaterials Applications for Nanomedicine; Pignatello, R., Ed., InTech: Rijeka, Croatia, 2011; pp. 17-58.

Lynn A K, Yannas I V, Bonfield W. Antigenicity and immunogenicity of collagen. J Biomed Mater Res B Appl Biomater. 2004 Nov. 15; 71(2):343-54.

Elzoghby A O. Gelatin-based nanoparticles as drug and gene delivery systems: reviewing three decades of research. J Control Release. 2013 Dec. 28; 172(3):1075-91. doi: 10.1016/j.jconrel.2013.09.019. Epub 2013 Oct. 2.

Giannandrea M, Parks W C. Diverse functions of matrix metalloproteinases during fibrosis. Dis Model Mech. 2014 Feburary; 7(2):193-203. doi: 10.1242/dmm.012062.

Anselmo A C, Modery-Pawlowski C L, Menegatti S, Kumar S, Vogus D R, Tian L L, Chen M, Squires T M, Sen Gupta A, Mitragotri S. Platelet-like Nanoparticles: Mimicking Shape, Flexibility, and Surface Biology of Platelets To Target Vascular Injuries. ACS Nano. 2014 Nov. 25; 8(11): 11243-53. doi: 10.1021/nn503732m. Epub 2014 Oct. 24.

Buckley J J, Gai P L, Lee A F, Olivi L, Wilson K. Silver carbonate nanoparticles stabilised over alumina nanoneedles exhibiting potent antibacterial properties. Chem Commun (Camb). 2008 Sep. 14; (34):4013-5. doi: 10.1039/b809086f. Epub 2008 Jul. 17.

Deacon J, Abdelghany S M, Quinn D J, Schmid D, Megaw J, Donnelly R F, Jones D S, Kissenpfennig A, Elborn J S, Gilmore B F, Taggart C C, Scott C J. Antimicrobial efficacy of tobramycin polymeric nanoparticles for Pseudomonas aeruginosa infections in cystic fibrosis: Formulation, characterisation and functionalisation with dornase alfa (DNase). J Control Release. 2014 Dec. 4; 198C:55-61. doi: 10.1016/j.jconrel.2014.11.022. [Epub ahead of print]

Hassan M S, Amna T, Yang O B, El-Newehy M H, Al-Deyab S S, Khil M S. Smart copper oxide nanocrystals: synthesis, characterization, electrochemical and potent antibacterial activity. Colloids Surf B Biointerfaces. 2012 Sep. 1; 97:201-6. doi: 10.1016/j.colsurfb.2012.04.032. Epub 2012 Apr. 28.

Nan D N, Fernandez-Ayala M, Fariñas-Alvarez C, Mons R, Ortega F J, González-Macias J, Fariñas M C. Nosocomial infection after lung surgery: incidence and risk factors. Chest. 2005 October; 128(4):2647-52.

Allen M S, Wood D E, Hawkinson R W, Harpole D H, McKenna R J, Walsh G L, Vallieres E, Miller D L, Nichols F C 3rd, Smythe W R, Davis R D; 3M Surgical Sealant Study Group. Prospective randomized study evaluating a biodegradable polymeric sealant for sealing intraoperative air leaks that occur during pulmonary resection. Ann Thorac Surg. 2004 May; 77(5): 1792-801.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

What is claimed is:

1. A tissue adhesive comprising a light activated methacryloyl-substituted gelatin, a photoinitiator, and a pharmaceutically acceptable carrier, wherein the methacryloyl-substituted gelatin is present at a concentration between 20% and 40% (w/v), and wherein the tissue adhesive has a burst pressure of at least 10 kPa when the methacryloyl-substituted gelatin is cross-linked by photo-irradiation.

2. The tissue adhesive of claim 1, wherein the methacryloyl-substituted gelatin has a degree of methacryloyl substitution between 50% and 90%.

3. The tissue adhesive of claim 1, wherein the methacryloyl-substituted gelatin is present at a concentration between 20% and 35% (w/v).

4. The tissue adhesive of claim 1, wherein the photoinitiator is selected from the group consisting of: 1-[4-(2-hydroxyethoxy)-phenyl]-2-hydroxy-2-methyl-1-propane-1-one, azobisisobutyronitrile, benzoyl peroxide, di-tert-butyl peroxide, 2,2-dimethoxy-2-phenylacetophenone, Eosin Y, and any combination thereof.

5. The tissue adhesive of claim 1, further comprising:
   a hemostatic agent selected from the group consisting of blood coagulation factors, prothrombin, thrombin, silicate nanoparticles, and any combination thereof; or
   (ii) an antibacterial agent selected from the group consisting of silver nanoparticles, copper oxide nanoparticles, nanoparticle-carried antibiotic drugs, penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim sulfamethoxazole, chitosan, and any combination thereof.

6. The tissue adhesive of claim 1, wherein the methacryloyl-substituted gelatin further comprises dopamine conjugated to the gelatin.

7. The composition of claim 1, wherein the methacryloyl-substituted gelatin is present at a concentration between 25% and 35% (w/v).

8. The composition of claim 1, wherein the methacryloyl-substituted gelatin is present at a concentration of about 25% (w/v).

9. A method for adhering or sealing soft tissue, comprising the steps of:
   a. Applying the tissue adhesive of claim 1 to the soft tissue to be adhered or sealed; and
   b. Exposing the composition to UV or visible light for a time sufficient to cross-link the methacryloyl-substituted gelatin to produce a tissue adhesive that has a burst pressure of at least 10 kPa.

10. The method of claim 9, wherein the soft tissue is a highly stressed elastic tissue.

11. The method of claim 9, wherein the method provides a seal against leakage of a fluid through the soft tissue.

12. The method of claim 9, wherein the composition is exposed to UV or visible light for a time period between 3 minutes and 5 minutes.

13. The method of claim 9, wherein the method does not comprise suturing or stapling the soft tissue to be adhered or sealed.

* * * * *

UNITED STATES PATENT AND TRADEMARK OFFICE
CERTIFICATE OF CORRECTION

Page 1 of 1

PATENT NO. : 10,814,032 B2
APPLICATION NO. : 15/502347
DATED : October 27, 2020
INVENTOR(S) : Alireza Khademhosseini, Nasim Annabi and Alexander Assmann It is certified that error appears in the above-identified patent and that said Letters Patent is hereby corrected as shown below:

In the Claims

In Column 28, Line 5, Claim 5, delete "a" and insert -- (i) a --

In Column 28, Lines 12-13, Claim 5, delete "tetracyclins," and insert -- tetracyclines, --

In Column 28, Line 20, Claim 7, delete "composition," and insert -- tissue adhesive --

In Column 28, Line 23, Claim 8, delete "composition," and insert -- tissue adhesive --

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*